US012163876B2

(12) United States Patent
Henion et al.

(10) Patent No.: US 12,163,876 B2
(45) Date of Patent: Dec. 10, 2024

(54) MULTILAYER DEVICE FOR SEPARATING BLOOD COMPONENTS AND USES THEREOF

(71) Applicant: PARTNERSHIP FOR CLEAN COMPETITION, Colorado Springs, CO (US)

(72) Inventors: John Degree Henion, Trumansburg, NY (US); Imelda Ryona, Penn Yan, NY (US); Larry Donald Bowers, Southern Pines, NC (US)

(73) Assignee: PARTNERSHIP FOR CLEAN COMPETITION, Colorado Springs, CO (US)

( * ) Notice: Subject to any disclaimer, the term of this patent is extended or adjusted under 35 U.S.C. 154(b) by 0 days.

(21) Appl. No.: 17/738,871

(22) Filed: May 6, 2022

(65) Prior Publication Data
US 2022/0268675 A1 Aug. 25, 2022

Related U.S. Application Data

(63) Continuation of application No. 16/079,067, filed as application No. PCT/US2017/019405 on Feb. 24, 2017, now Pat. No. 11,326,992.
(Continued)

(51) Int. Cl.
*G01N 1/40* (2006.01)
*B01L 3/00* (2006.01)
(Continued)

(52) U.S. Cl.
CPC .......... *G01N 1/4077* (2013.01); *B01L 3/5023* (2013.01); *G01N 33/48* (2013.01);
(Continued)

(58) Field of Classification Search
CPC .... G01N 1/4077; G01N 33/48; G01N 33/491; G01N 33/56966; G01N 2001/288;
(Continued)

(56) References Cited

U.S. PATENT DOCUMENTS 5,273,888 A * 12/1993 Guadagno ............ G01N 33/528
436/66
5,369,007 A 11/1994 Kidwell
(Continued)

FOREIGN PATENT DOCUMENTS

CN 202330105 U 7/2012
CN 104519975 A 4/2015
(Continued)

OTHER PUBLICATIONS

Barnes AJ et al., Next Generation plasma collection technology for the clinical analysis of tem. zolomide by HI IC/ MS/MS. A technical product review. Shimadzu, [Retrieved online Apr. 12, 20171 <URL:https://novilytiocom/wp-content'uploads12015/05/Shimadzu-Workflow-fonTemozolomide . . . pdf> Jun. 2014: p. 2, col. 1, first-second paragraphs and figure 1; p. 3, figures 1-2.
(Continued)

*Primary Examiner* — Dennis White
(74) *Attorney, Agent, or Firm* — Loeb & Loeb LLP

(57) ABSTRACT

Embodiments of the invention are generally directed to analyte detection and products facilitating the collection, separation of sample components, and analyte detection. The multilayer device that allows for a rapid, easy, accurate, and efficient test of a fluid sample for analytes of interest and methods of collecting, separating components, and testing using the multilayer device are described in various embodiments of the invention.

15 Claims, 11 Drawing Sheets

Related U.S. Application Data

(60) Provisional application No. 62/299,226, filed on Feb. 24, 2016.

(51) Int. Cl.
  *G01N 1/28* (2006.01)
  *G01N 33/48* (2006.01)
  *G01N 33/49* (2006.01)
  *G01N 33/569* (2006.01)

(52) U.S. Cl.
  CPC ..... *G01N 33/491* (2013.01); *G01N 33/56966* (2013.01); *B01L 2300/0681* (2013.01); *B01L 2300/0816* (2013.01); *B01L 2300/165* (2013.01); *G01N 2001/288* (2013.01); *G01N 2001/4088* (2013.01)

(58) Field of Classification Search
  CPC .......... G01N 2001/4088; B01L 3/5023; B01L 2300/0681; B01L 2300/0816; B01L 2300/165
  See application file for complete search history.

(56) References Cited

U.S. PATENT DOCUMENTS

| | | | |
|---|---|---|---|
| 5,733,507 A | 3/1998 | Zakim | |
| 6,036,659 A | 3/2000 | Ray | |
| 6,106,732 A * | 8/2000 | Johnston | G01N 33/491 210/508 |
| 11,326,992 B2 | 5/2022 | Henion | |
| 2014/0295415 A1 | 10/2014 | Rolland | |
| 2019/0049353 A1 | 2/2019 | Henion | |

FOREIGN PATENT DOCUMENTS

| | | |
|---|---|---|
| CN | 106132543 A | 11/2016 |
| EP | 0418765 A2 | 3/1991 |
| JP | 2005274497 A | 10/2005 |
| JP | 2008275627 A | 11/2008 |
| KR | 20130142768 A | 12/2013 |
| WO | 2009075709 A1 | 6/2009 |
| WO | 2012015926 A2 | 2/2012 |
| WO | 2013191361 | 12/2013 |
| WO | 2015095853 | 6/2015 |
| WO | WO-2016070971 A1 * | 5/2016 ................ B01L 9/52 |

OTHER PUBLICATIONS

Barnes et al., "Next generation plasma collection technology for the clinical analysis of temozolomide by HILIC/MS/MS", Shimadzu Corporation, Jun. 1, 2014, pp. 1-6, XP055413344, retrieved from the internet: URL: https://novilytic.com/wp-content/uploads/2015/05/Shimadzu-Workflow-for-Temozolomide.pdf (retrieved on Oct. 6, 2017).

Chinese Office Action (with English translation) for App. No. CN201780024862.X, dated Dec. 2, 2020, 28 pages.

Extended European Search Report for Application No. EP17757324.3, dated Jun. 19, 2019, 12 pages.

International Search Report, corresponding o International Application No. PCT/US2017/14905, dated May 19, 2017 (3 pages).

Japanese Office Action (including English translation) for App. No. JP2018-545317 dated Nov. 4, 2020, 4 pages.

Office Action (Notice of Allowance and Fees Due (PTOL-85)) dated Jan. 7, 2022 for U.S. Appl. No. 16/079,067 (pp. 1-8).

Office Action (Notice of Allowance and Fees Due (PTOL-85)) dated Jan. 18, 2022 for U.S. Appl. No. 16/079,067 (pp. 1-5).

Office Action (Notice of Allowance and Fees Due (PTOL-85)) dated Feb. 24, 2022 for U.S. Appl. No. 16/079,067 (pp. 1-4).

Office Action dated Aug. 11, 2021 for U.S. Appl. No. 16/079,067 (pp. 1-22).

Sturm et al., "Novel membrane devices and their potential utility in blood sample collection prior to analysis of dried plasma spots", 2015, Bioanalysis, vol. 7, No. 16, pp. 1987-2002.

Written Opinion of the International Searching Authority, corresponding to International Application No. PCT/US2017/14905, dated May 19, 2017 (9 pages).

Canadian Office Action issued in App. No. CA3015627, dated Jan. 24, 2023, 6 pages.

* cited by examiner

A

B

A

B

C

MULTILAYER DEVICE FOR SEPARATING BLOOD COMPONENTS AND USES THEREOF

CROSS-REFERENCE TO RELATED APPLICATIONS

This application is a continuation of U.S. application Ser. No. 16/079,067, filed on Aug. 22, 2018, which is a National Phase entry of PCT/US2017/019405, filed Feb. 24, 2017, which claims the benefit of U.S. Provisional Patent Application No. 62/299,226, filed Feb. 24, 2016, entitled, "Dried Plasma Spot Card For Automated Online Determination Of Opioids," all of which are incorporated by reference herein in their entirety.

FIELD OF INVENTION

This invention relates generally to separation of fluid sample components for analyte detection. More particularly, aspects of the invention are directed to a facile and accurate device for separation of various components of whole blood, including but not limited to red blood cells, white blood cells, platelets, and plasma, using a multilayer device or multilayer separation device for the separation of blood components and methods of using such device to detect analytes in the various blood components, for example, specifically on the cell surface and in the intra- and extra-cellular fluids, such as, but not limited to, chemical compounds, drugs and metabolites, nucleic acids, DNA, RNA, mRNA, miRNA, proteins, cell surface and intracellular markers, pathogens, bacteria, viruses, microorganisms, and the like.°

DESCRIPTION OF RELATED ART

Sporting events have united people of all ages and nationalities. Integrity of the games and athletes must be guarded to safeguard the powerful positive impacts of sports. To maintain that integrity, testing systems must evolve to give the public confidence that the athletes are not illegally using performance enhancing drugs. In addition to competitive athletic testing, chemical substance testing is often administered to prospective or current employees, prisoners or parolees, military personnel, in post-vehicular, aviation, and boating accidents, in forensics analyses, and the like. For example, dried blood spot technology has been used to screen newborn infants for congenital metabolic diseases. Although sampling is advantageously achieved by a finger or heel stick to obtain a minimal volume, easy transport and sample stability, there are still several obstacles.

The available products and testing methods have many challenges with respect to limitations in sample collection and processing, sample yields, hematocrit (Hct) compatibility, and spectrophotometric detection. One post-collection analyses issue is the limitation of processing the collected sample, which involves manual manipulation and detection from a hole punch by manually removing the dried blood spot, punching a small portion of the dried blood spot (about 3 millimeters-6 millimeters), and eluting the smaller sample in solvent for standard analyses. This is not an automated process.

Two existing dried plasma spot (DPS) cards are the NOVIPLEX™ card, which is commercially available from Novilytic LLC (Kim, J. H., et al. *Anal Chem* 2013, 85, 11501-11508) and the 'auto DPS card' previously reported by Sturm et al. (*Bioanalysis* 2015, 7, 1987-2002). The functionality of the plasma collection substrate which is the collection material or cellulose paper is a key difference among the various dried spot cards. The auto DPS card has a wax boundary. With the wax boundary of the auto DPS card, the excess filtered plasma is retained within the boundary resulting in inaccuracy biases at the low and high ends of the hematocrit. At a low hematocrit level, more plasma is available and retained within the wax bound area while at high hematocrit levels, less plasma is retained. The boundary of the NOVIPLEX™ card is different from the wax boundary described in the auto DPS card. The NOVIPLEX™ card has a disk that once saturated, the excess filtered plasma freely flows outside of or beyond the disk. This action is unlike the auto DPS card where excess plasma is trapped within the boundary. In general, the conceptual design of these two cards are similar as each of them employs an on-card membrane filtration technique to separate RBC from plasma. However, the card structures and production of plasma in each card format are different and each has its own disadvantages. As described above, the auto DPS card may not be accurate nor efficient. The auto DPS card reportedly may utilize a sample support device also known as the Liquid Extraction Surface Analysis, LESA™, stage by Advion, Inc. (Ithaca, NY USA). Although the NOVIPLEX™ card does not require any external device for generation of plasma spots, it is not compatible for automated analysis. As a result, the sample handling process is tedious requiring a pair of tweezers to remove a small 2-mm filter disk containing the sample and manually transferring the disk for further sample extraction processes. While the yield of plasma volume by auto DPS was not determined, the NOVIPLEX™ card requires a minimum of 25 µL blood to produce about 2.5 µL plasma (Kim, J. H. et al. *Anal Chem* 2013, 85, 11501-11508). The yield of plasma volume is unfortunately low, i.e., 0.100 µL plasma per µL blood. The plasma yield from the NOVIPLEX™ card is about 2.5 µL, which is insufficient for most analyses. The low quantity of plasma is not due to a low initial blood sample volume, rather it is due to a limited capacity of the plasma collection substrate. Scaling up is not possible.

Therefore there is a need for a facile, accurate, efficient, and rapid system for separating components of a sample and detecting analytes, such as but not limited to a manual or an automated system. More particularly, there is a need for a product and technique that utilizes a simplified sample collection process, reduced costs, and simplified shipping and storage that overcomes the need for centrifugation to separate components of whole blood (Sturm, et al. *Bioanalysis* 2015, 7, 1987-2002 ("Sturm"); Kim et al. *Anal Chem* 2013, 85, 11501-11508 ("Kim"); Li et al. *Rapid Commun Mass Spectrom* 2012, 26, 1208-1212 ("Li")), narrow hematocrit range presently available for testing, i.e., Hct 40-55% (Sturm), low yield of plasma volume (Sturm; Kim; Li), and lack of fully automated analyses (Kim; Li).

BRIEF SUMMARY OF THE INVENTION

In one embodiment, the invention provides a multilayer device for collection and separation of, for example, blood components, allowing for the detection of analytes from a fluid sample applied to the multilayer device, for example whole blood. The multilayer device may be a dried spot card composed in a book-type form in one embodiment, where there is a top and bottom cover hinged on one edge forming a spine and sandwiching multiple layers of membranes and materials similar to the pages of a book. Alternatively, more than one or all of the edges are temporarily connected or coupled, and any or all of the layers of the multilayer device that are connected or coupled on one or more edges, may be detached, removed, or separated from each other and from the device. Separation of the fluid sample allows for subsequent individual analyses of the separated components.

Another aspect may be directed to a multilayer device comprising layers that may be separately removed or detached as desired. A multilayer device having a rectangular shape, may be temporarily attached or coupled on all edges, where any or all layers of the multilayer device may be detached or removed. For example, the edges of any or all of the layers may be perforated in such a manner that allows for the layer to be torn out or detached from the remaining components of the multilayer device. Alternatively, the layers may be tightly sandwiched between the top and bottom covers in such a manner that the fluid sample does not leak and each of the layers of the multilayer device remain in position until separated for removal.

One aspect is directed to a multilayer device, comprising
a) a top unit, wherein said top unit comprises a filtration membrane unit adjacent to a hydrophobic membrane; and
b) a bottom unit, wherein said bottom unit comprises a collection material and a bottom cover,
where said top unit is adjacent to and connected to said bottom unit, said filtration membrane unit comprising at least one filtration membrane, said filtration membrane unit has a top surface and a bottom surface, and said hydrophobic membrane has a top surface and a bottom surface, where said bottom surface of said filtration membrane unit is adjacent to said top surface of said hydrophobic membrane, where said collection material has a top surface and a bottom surface, said bottom surface of said hydrophobic membrane is adjacent to said top surface of said collection material, and said bottom surface of said collection material is adjacent to said bottom cover.

Another aspect provides a multilayer device, comprising:
a) a top unit comprising layers of: a top cover with at least one cutout, a filtration membrane unit, and a hydrophobic membrane with at least one cutout and the same number of cutouts as in the top cover; and
b) a bottom unit comprising layers of: a collection material and a bottom cover without cutouts,
where said top unit is adjacent to and connected to said bottom unit, said filtration membrane unit comprises at least one filtration membrane, preferably two filtration membranes of decreasing pore sizes with each having, in one aspect, a shape of said cutout, said filtration membrane unit is positioned within said cutout of said top cover and adjacent to said hydrophobic membrane, where each of the layers of the top cover, filtration membrane unit, and hydrophobic membrane are aligned by the cutouts, said hydrophobic membrane is adjacent to or sandwiched between said filtration membrane unit and said collection material, said collection material is adjacent to said hydrophobic membrane, and said collection material is above said bottom cover. Since plasma is primarily water, a hydrophobic material will not absorb any plasma. A hydrophobic membrane that has cutouts will prevent any plasma from leaking or spreading beyond the boundaries of the cutouts, thus enabling a dried spot positioned centrally within the cutouts. The filtration membrane unit in one aspect may be sandwiched between the top cover and the hydrophobic membrane. The collection material, which is an absorptive layer such as cellulose, paper, etc., in another aspect may be sandwiched between said hydrophobic membrane and said bottom cover. The multilayer device may be in the shape of rectangle having four edges, where each of the layers of the top unit or the bottom unit is temporarily coupled on at least one edge, forming a sufficiently tight contact to avoid any leakage or movement of layers, and each of the layers of the top unit and the bottom unit is detachable or removable. An alternative format of a multilayer device further includes a contact support layer adjacent to and below said collection material and adjacent to or above said bottom cover, or contact supports form a portion of a bottom cover, where contact supports of the contact support layer preferably contains raised supports where at least a portion of said raised supports fits within the cutout where a fluid sample is placed. A further aspect comprises said multilayer device which may also include at least one window support for a layer detached for subsequent analyses, preferably for a filtration membrane unit and/or a collection material. The window support may be a layer containing a window which exposes the sample for detecting an analyte of interest, said layer for subsequent analyses is attached or coupled to said window support, and said window support coupled to said layer for subsequent analyses may be removed or detached from said multilayer device for subsequent biological analyses.

A further aspect is directed to a multilayer device comprising: a top unit comprising layers of: a top cover with at least one cutout, a filtration membrane unit, and a hydrophobic membrane with at least one cutout; and
b) a bottom unit comprising layers of: a collection material and a bottom cover without cutouts,
In other aspects, a method of using the multilayer device comprises:
a) applying a flexible volume of a fluid to a multilayer device comprising
(i) a top unit comprising layers of a top cover with at least one cutout or open hole on or in which a fluid sample is placed, a filtration membrane unit, and a hydrophobic membrane: and
(ii) a bottom unit comprising layers of a collection material and a bottom cover without cutouts, where said top unit is adjacent to said bottom unit, where said volume may be about 10 microliters to about 100 microliters;
b) waiting for about 3 minutes with said top unit in contact with said bottom unit:
c) separating said filtration membrane unit and/or said collection material from said multilayer device;
d) waiting for about 30 minutes while said separated filtration membrane unit and/or said collection material dry; and
e) analyzing said filtration membrane unit and/or said collection material. The analysis of said filtration membrane unit and/or said collection material may include detecting an analyte of interest.

A further aspect of may be directed to a method of using the multilayer device, comprising:
a) applying a volume of a fluid sample to said filtration membrane unit of said multilayer device;
b) waiting for about 3 minutes with said top unit in contact with said bottom unit, and
c) storing said multilayer device. After storage of the multilayer device from a few minutes to several days with or without transporting the multilayer device to a facility for analysis, the multilayer device containing a secure and tamper-proof sample undergoes further manipulation. After storing the multilayer device, the method of using further comprises:
d) separating the filtration membrane unit and the collection material from the multilayer device; and e) analyzing the filtration membrane unit and/or the collection material for analytes of interest,
where the multilayer device may be a 3D-printed device or a non-3D-printed device, e.g., card stock.

The benefits of the multilayer device and techniques described here include simplified sample collection, reduced costs, simplified shipping and storage, and a gained significant interest in various fields (Tretzel, L. et al. *Analytical Methods* 2015, 7, 7596-7605; Sadones, N. et al. *Bioanalysis* 2014, 6, 2211-2227). The inventive multilayer device overcomes many challenges in the art including the hematocrit effect and sampling of whole blood instead of plasma (De Kesel, P. M. et al. *Bioanalysis* 2013, 5, 2023-2041).

In another aspect, a multilayer device is configured for facile and rapid detection analyses of analytes found in dried sample spots collected and separated by the multilayer device, such as but not limited to automated, high-throughput analyses. Therefore, the inventive multilayer device described here was developed to be compatible for a wide range of hematocrit levels (e.g., 25%-65%), a high plasma volume yield from a whole blood fluid sample, and separate analyses of multiple components of a single fluid sample.

BRIEF DESCRIPTION OF THE DRAWINGS

The invention may be better understood by references to the detailed description when considered in connection with the accompanying drawings. The components in the figures are not necessarily to scale, emphasis instead being placed upon illustrating the principles of the invention. In the figures, like reference numerals designate corresponding parts throughout the different views.

The invention relates in part to an improved dried spot card. Among other fields and applications, the invention may have utility in, for example, detecting chemical compounds, drugs, metabolites, hormones, opioids, viruses, nucleic acids, proteins, and the like, from a fluid sample, including, but not limited to, whole blood, red blood cells, plasma, and platelets. The use of the multilayer device may also be contemplated for detecting analytes of interest in fluid samples that do not necessarily require separation, such as for example, urine, saliva, tears, amniotic fluid, semen, and the like.

The figures depict aspects of a multilayer device, including fluid sample separation and determination of the presence of chemical compounds, drugs, opioids, hormones, nucleic acids, proteins, and the like, in accordance with example embodiments.

Figure 1:
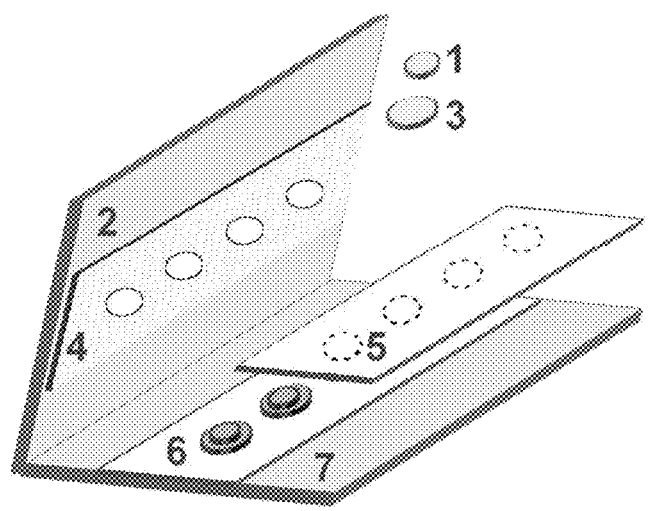

FIG. 1 shows a book-type multilayer device, where the numbers indicate the assembly order from 1 to 6, which are described in detail in Example 1.

Figure 2:
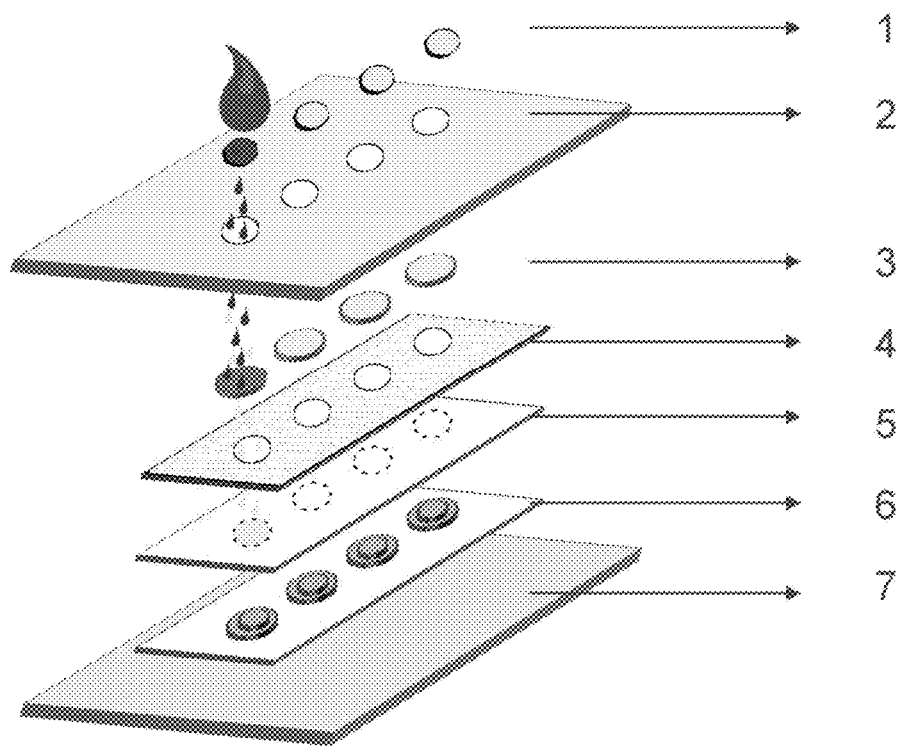

FIG. 2 shows a multilayer device containing seven layers: (1) a first filtration membrane that fits within each cutout; (2) a top cover with four cutouts: (3) a second filtration membrane that fits within each cutout and adjacent to the first filtration membrane; (4) a hydrophobic membrane containing cutouts; (5) a collection material without cutouts, and optionally having an outline of the cutout perimeter where the cutouts are located; (6) a contact support layer; and (7) a bottom cover.

Figure 3:
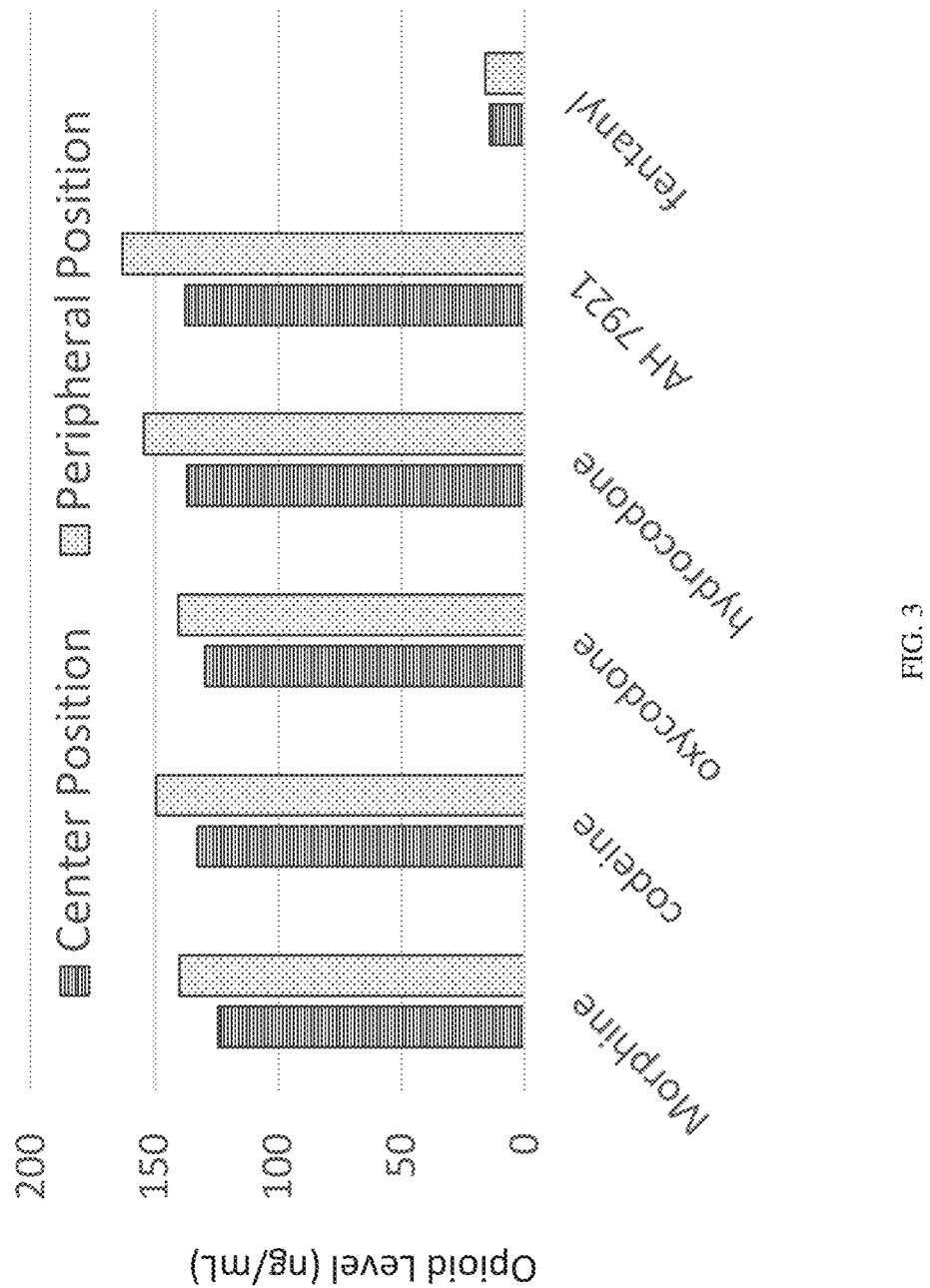

FIG. 3 shows the results of center and peripheral sampling positions for various opioids, where the left column and the right column for each opioid represent a center position and a peripheral position, respectively.

Figure 4:
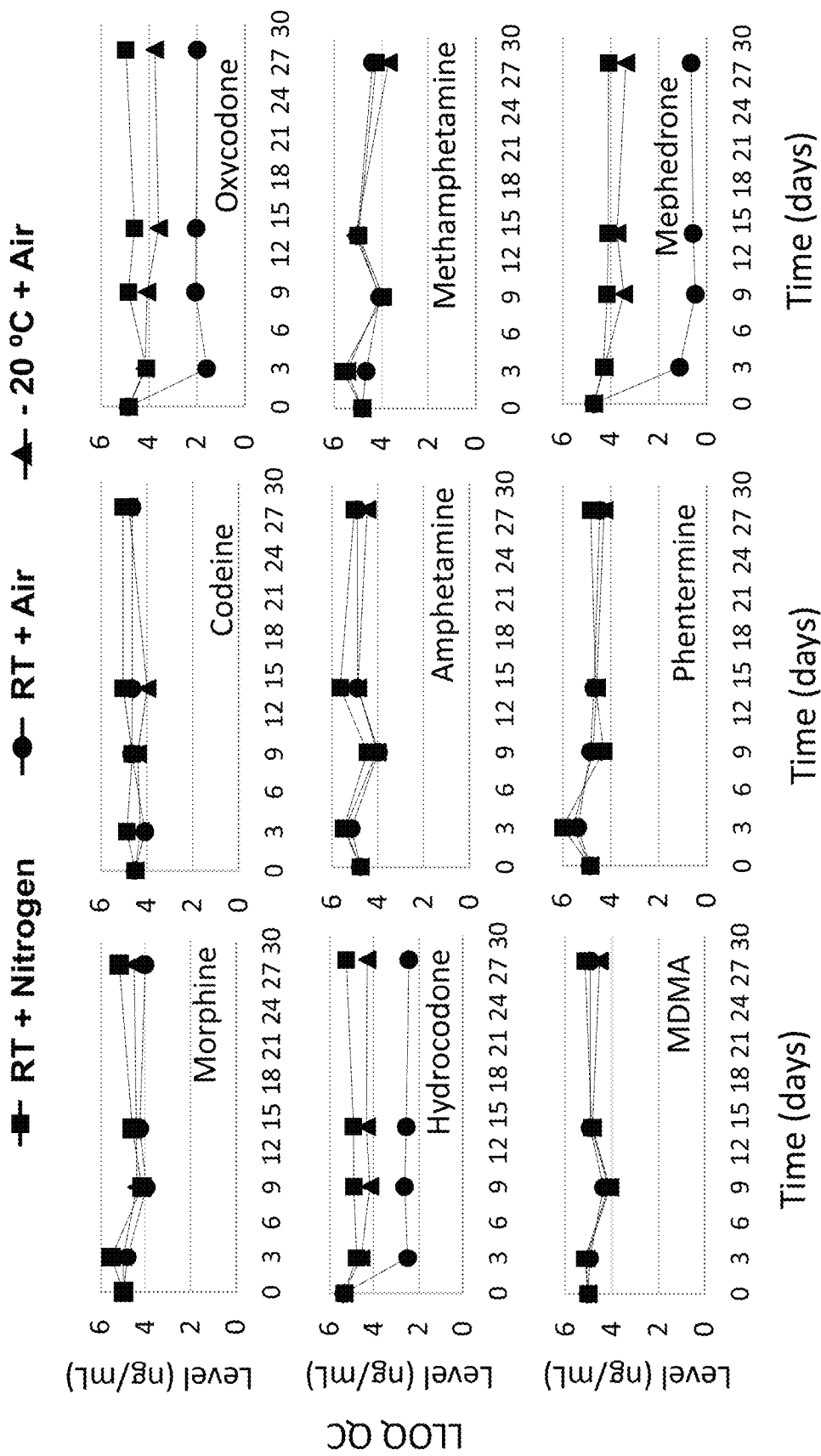

FIG. 4 shows on-card stability of opioids and stimulants at LLOQ (5 ng/mL) at three different storage conditions: at RT kept in a box filled with a continuous flow of nitrogen (RT+Nitrogen), at RT kept in a glassine envelope+desiccant further sealed in a Ziploc bag (RT+Air), and at −20° C. kept in a glassine envelope+desiccant further sealed in a Ziploc bag (−20° C.+Air).

Figure 5:
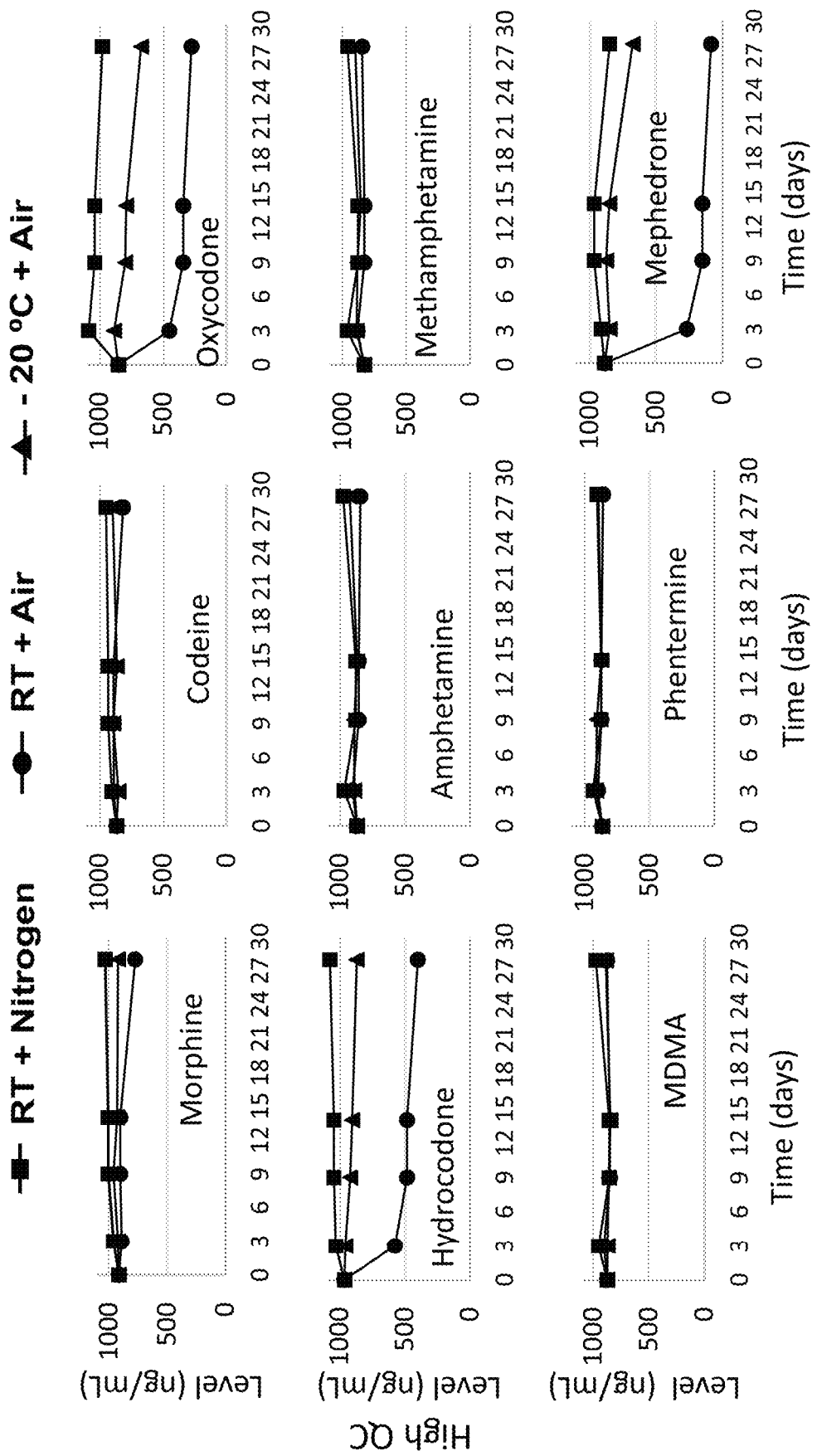

FIG. 5 shows on-card stability of opioids and stimulants at High QC (900 ng/mL) at three different storage conditions: at RT kept in a box filled with a continuous flow of nitrogen (RT+Nitrogen), at RT kept in a glassine envelope+desiccant further sealed in a Ziploc bag (RT+Air), and at −20° C. kept in a glassine envelope+desiccant further sealed in a Ziploc bag (−20° C.+Air).

Figure 6:
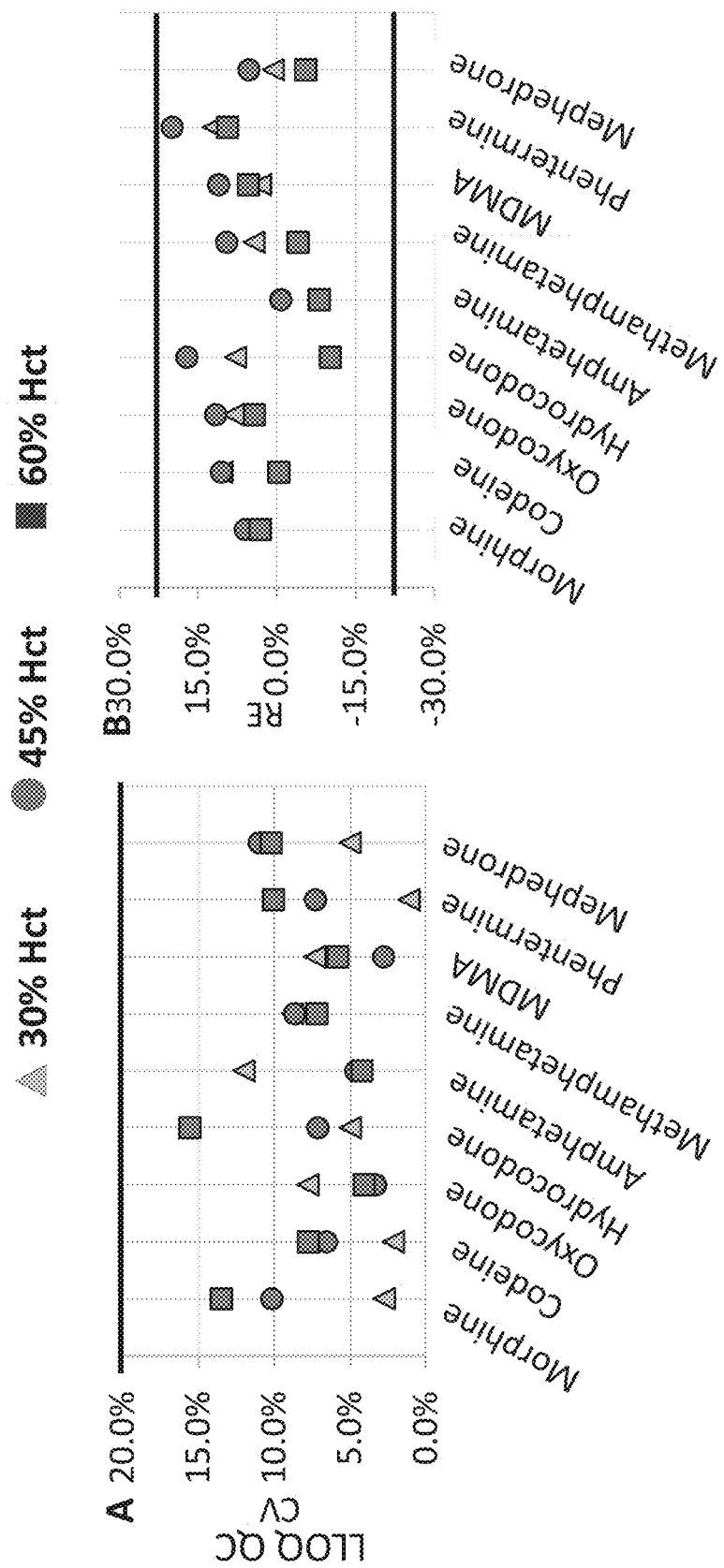
Figure 6:
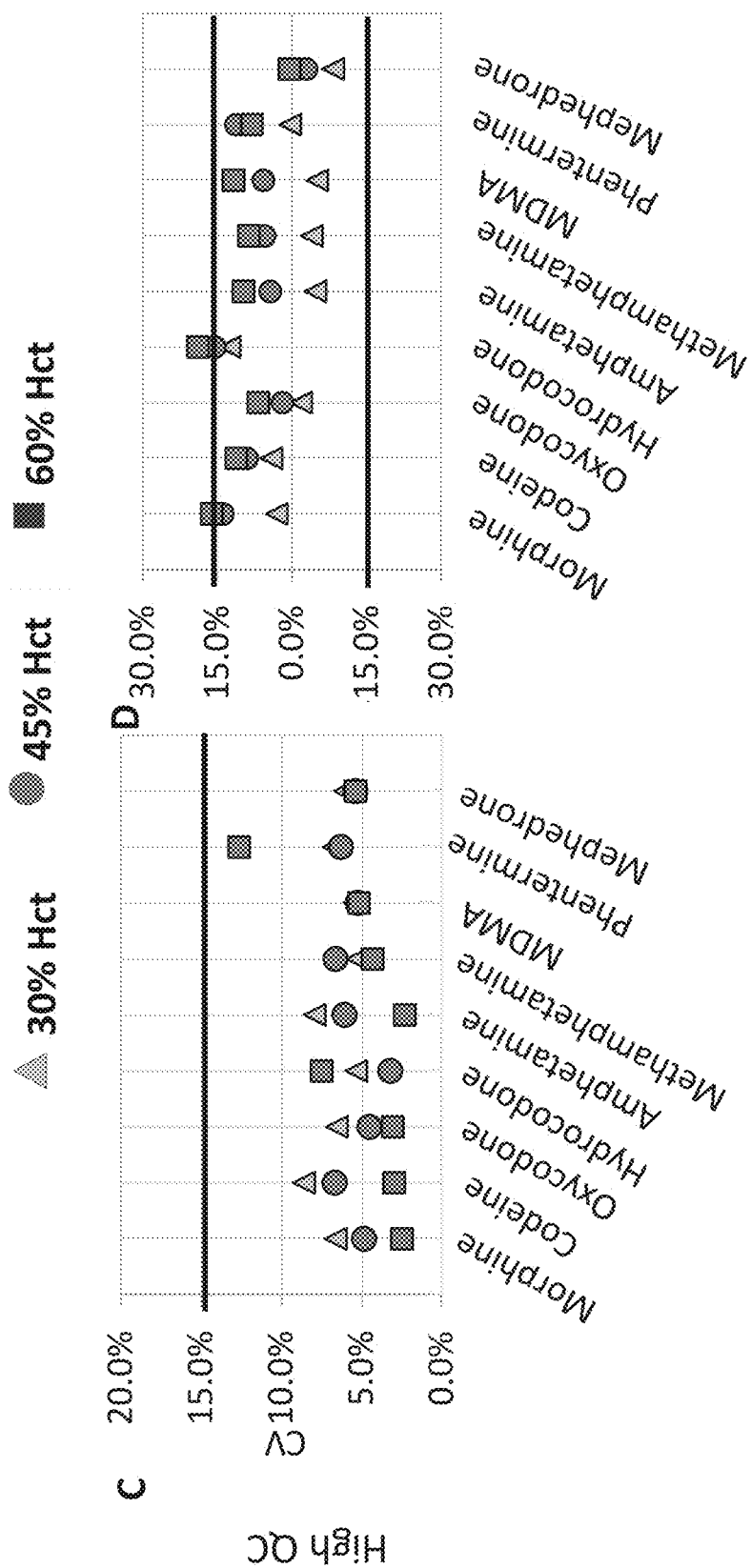

FIG. 6 shows precision and accuracy for multilayer device analysis using blood with 30%, 45%, and 60% Hct (n=3) at the LLOQ (A and B) and high QC (C and D).

Figure 7:
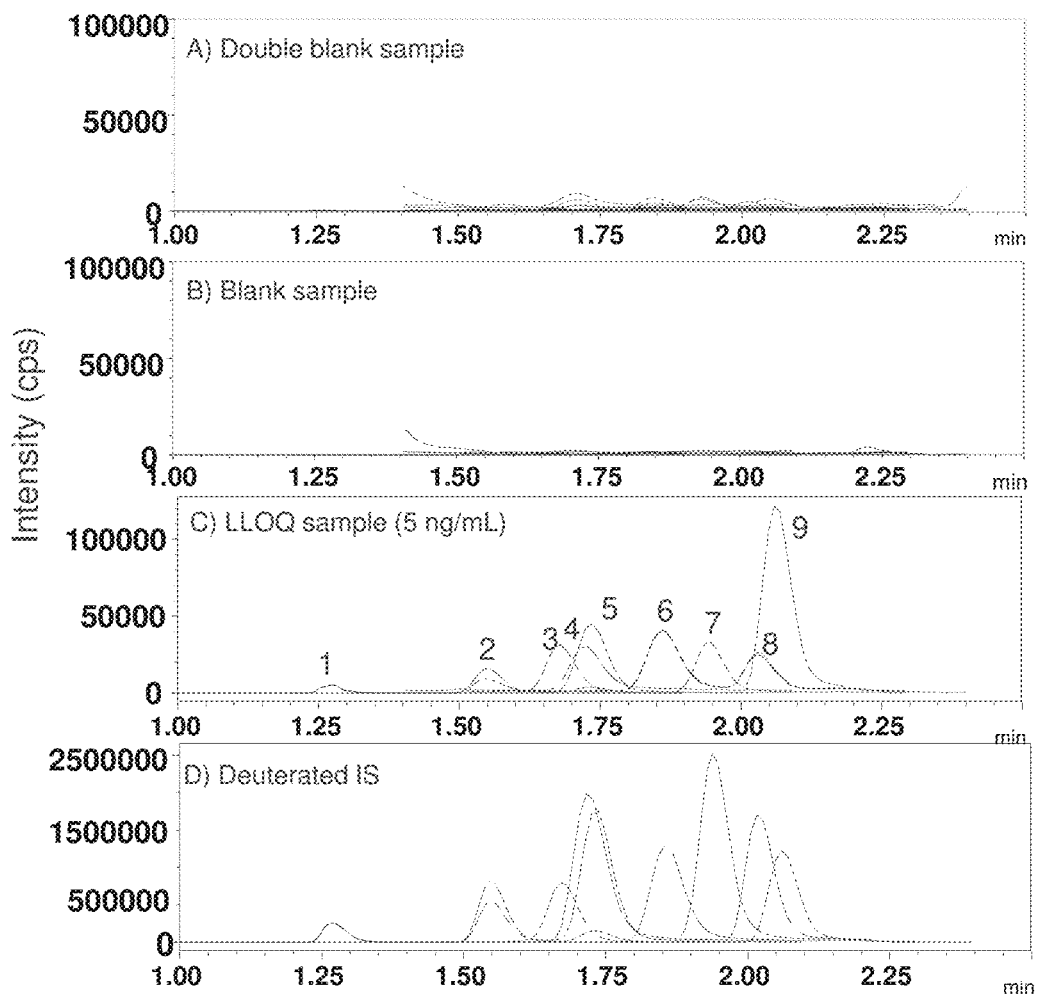

FIG. 7 shows SRM LC/MS chromatograms from fortified blood samples containing morphine (1), codeine (2), oxycodone (3), amphetamine (4), hydrocodone (5), methamphetamine (6), MDMA (7), phentermine (8), and mephedrone (9) for A) a blank sample (matrix blank without IS), B) a zero sample (matrix blank with IS, showing only analyte signals), C) LLOQ sample (matrix fortified with 5 ng/mL standards) and D) their deuterated IS.

Figure 8:
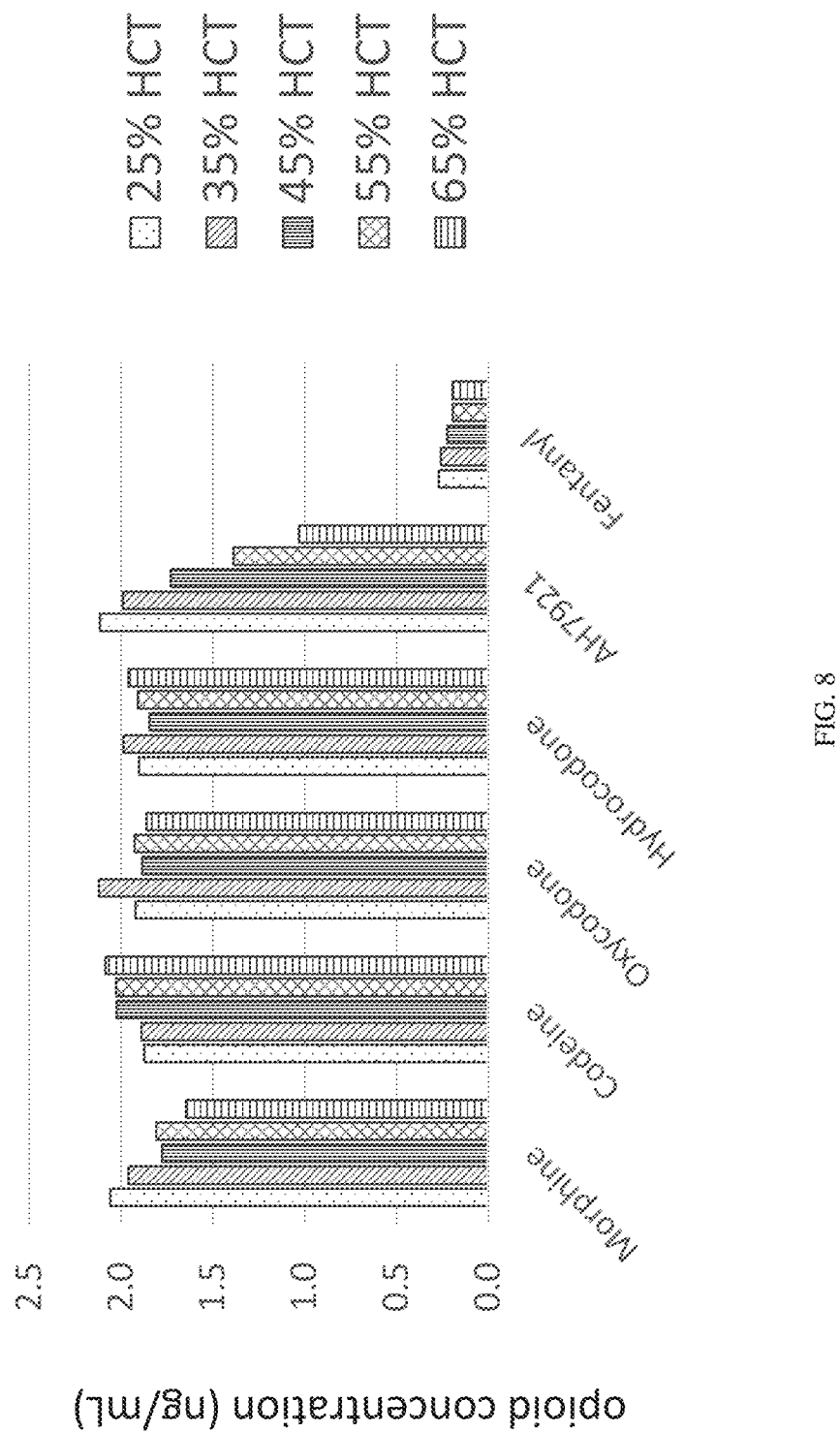

FIG. 8 shows the results of hematocrit levels of 25%-65% as tested for various opioids.

Figure 9:
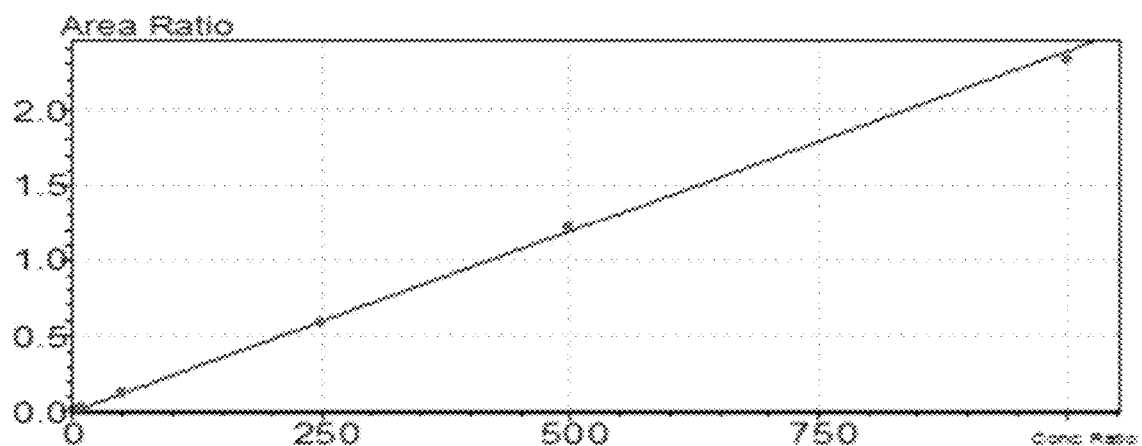
Figure 9:
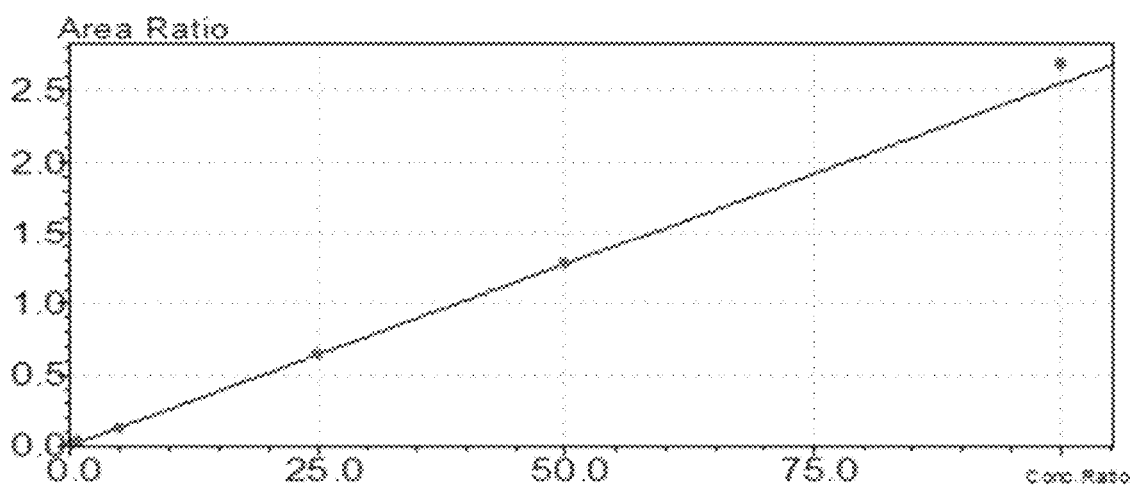

FIG. 9 shows linearity graphs for morphine (A) and fentanyl (B).

Figure 10:
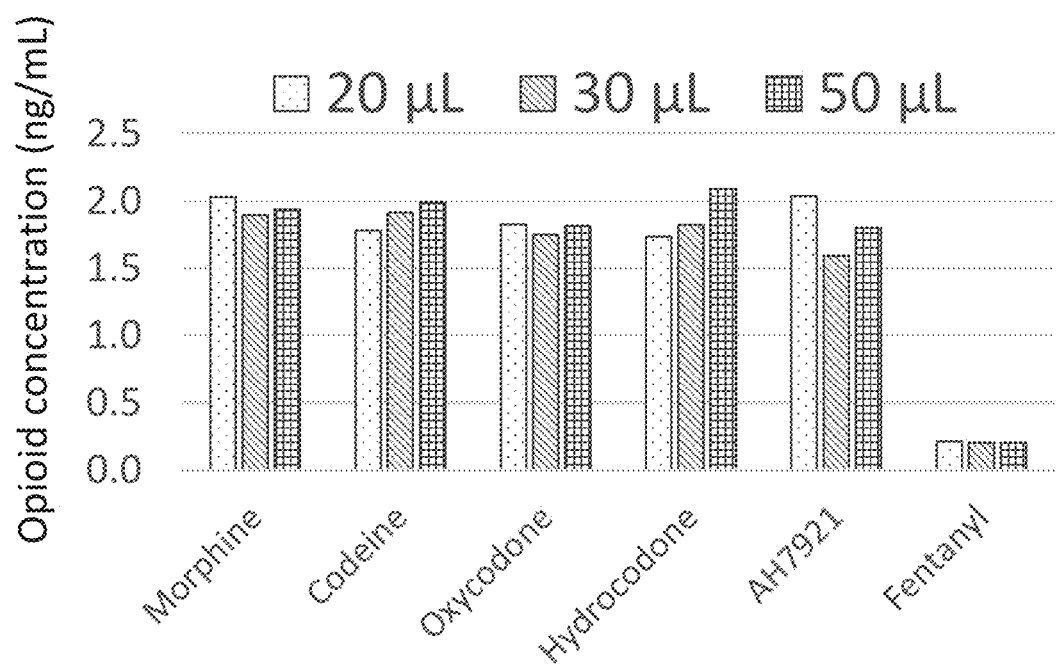

FIG. 10 shows a comparison of volumetric sampling from 20 µl-50 µl whole blood for various opioids.

Figure 11:
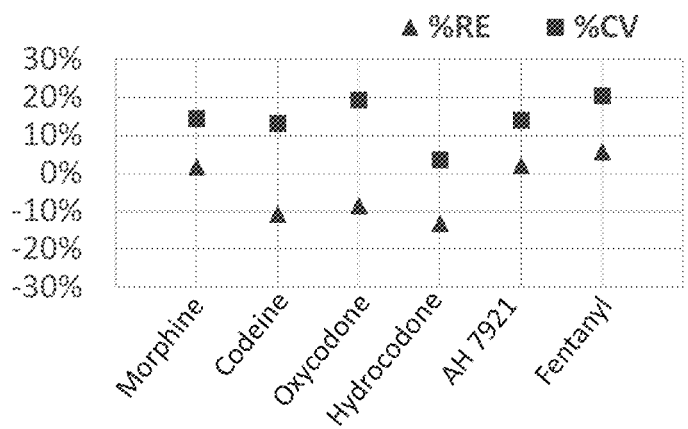
Figure 11:
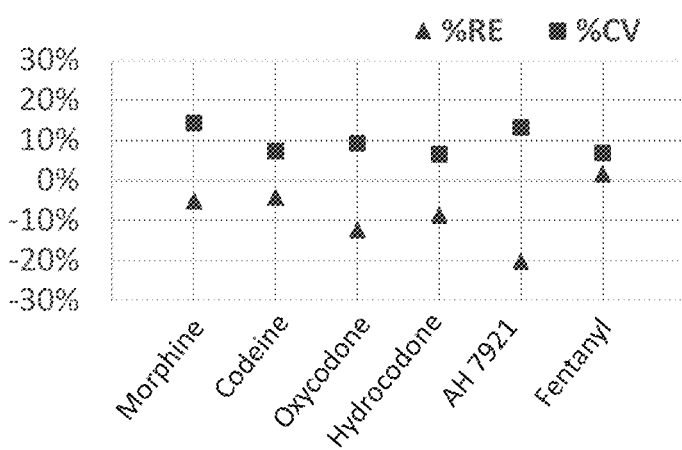
Figure 11:
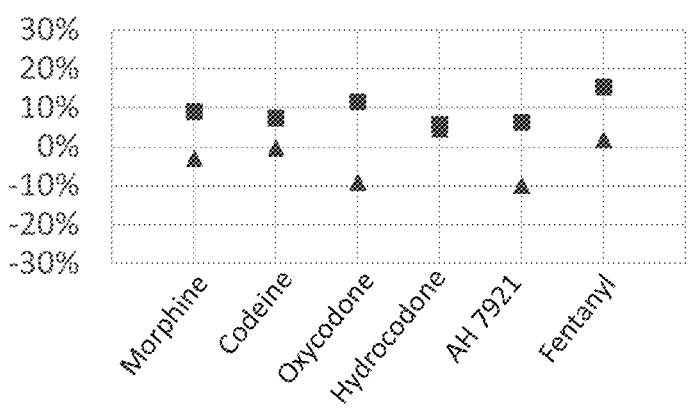

FIG. 11 shows the % RE and % CV for various opioids and for (A) 20 µl, (B) 30 µl, and (C) 50 µl whole blood.

Persons of ordinary skill in the art will appreciate that elements in the figures are illustrated for simplicity and clarity so not all connections and options have been shown to avoid obscuring the inventive aspects. For example, common but well-understood elements that are useful or necessary in a commercially feasible embodiment are not often depicted in order to facilitate a less obstructed view of these various embodiments of the present disclosure. It will be further appreciated that certain actions and/or steps may be described or depicted in a particular order of occurrence while those skilled in the art will understand that such specificity with respect to sequence is not actually required. It will also be understood that the terms and expressions used herein are to be defined with respect to their corresponding respective areas of inquiry and study except where specific meanings have otherwise been set forth herein.

DETAILED DESCRIPTION

The present invention now will be described more fully with reference to the accompanying drawings, which form a part hereof, and which show, by way of illustration, specific exemplary embodiments by which the invention may be practiced. These illustrations and exemplary embodiments are presented with the understanding that the present disclosure is an exemplification of the principles of one or more inventions and is not intended to limit any one of the inventions to the embodiments illustrated. The invention may be embodied in many different forms and should not be construed as limited to the embodiments set forth herein: rather, these embodiments are provided so that this disclosure will be thorough and complete, and will fully convey the scope of the invention to those skilled in the art.

As described here, the exemplary embodiments describe a multilayer device for separation of a fluid sample, for example, whole blood, and analyses of such fluid sample for analytes of interest. Essentially the multilayer device is a dried fluid spot device for micro-sampling, separating, and analyzing dried fluid spot samples. One embodiment of a multilayer device or multilayer device card comprises: (1) a filtration membrane unit with areas designated for fluid sample collection; (2) a support layer or top cover that is preferably labeled for sample identification; (3) a collection material: and (4) a support layer or bottom cover as exemplified in FIG. 2. A fluid sample is applied to the multilayer device, where the fluid sample may be any fluid, preferably a biological fluid, for testing for the presence of analytes. The fluid or fluid sample may include, but is not limited to, whole blood, red blood cells, plasma, plasma protein fraction, cerebral spinal fluid, or any fluid possibly containing an analyte of interest, and the like. One of skill in the art could modify components of the multilayer device accordingly to accommodate for the various fluids and desired analytes. For example, the filtration membrane sizes may be altered in order to capture or separate the analytes of interest.

Samples for dried spot cards available in the art have limitations, in particular, sample volume inconsistencies, which may negatively affect results. In dried blood spot (DBS) techniques, hematocrit (Hct)-dependent issues may be resolved by employing whole spot analysis which then leads to the need for an accurate spotting volume of the blood onto the card. This can be easily attained if sample collection and spotting are performed by trained personnel using an accurate sampling device such as, for example, a volumetric pipette. Alternative ways to collect known volumes of finger prick blood include a 'volumetric' capillary sampling system (DBS System; Gland, Switzerland) is incorporated by reference as disclosed in the art (Leuthold. L. A. et al. *Anal. Chem.* 2015, 87, 2068-2071; R. Verplaetse and J. Henion, *Anal. Chem.* 2016, 88, 6789-6796). The DBS system provides an accurate volume of 5.5 µL of whole blood from a finger prick. Alternatively, volumetric pipettes such as an EPPENDORF® pipette (Z683787 Aldrich: EPPENDORFX® Research® plus pipette, variable volume; 0.5 µL-10 µL; SIGMA-ALDRICH1@k CO) may be used or a glass capillary (P2174 Sigma; Microcapillary tube DRUMMOND MICROCAPS®; volume 50 µL).

Typically, if sample collection is to be performed by untrained personnel, it will pose a critical control point to assure that accurate sample volume has been collected. In the application of a multilayer device card described here, particularly such devices that have an intimate contact between layers, accurate sampling volume is not necessarily required to obtain accurate and precise quantitation. The multilayer device described here may accommodate a wide fluid sample volume range of up to about 50 microliters (µL) of, for example, whole blood and even up to about 100 µL while most of the commercially available or currently used devices may only handle single digit volumes of blood in microliters (e.g., 5 µL)

A book-type or other multilayer device card that allows for an intimate contact provides the feature of a flexible sampling volume. Plasma consistency was observed to be independent of the Hct level in blood as presented by Li et al. (*Journal of Chromatography B—Analytical Technologies in the Biomedical and Life Sciences* 2015, 991, 46-52). Based on studies in the Examples section, plasma generated from whole blood having hematocrit (Hct) levels of about 30% Hct or 60% Hct has the same spreading consistency on the paper substrate and thus produces homogenous spots. Homogenous spots do not equate to equal spot dimension. It refers to homogenous saturation of plasma within a spot regardless of the spot size. The inventive multilayer device described here is capable of handling and processing flexible volumes and a larger volume than that in the art, without adversely affecting results. In fact, a larger whole blood sample, which the described multilayer device provides may result in larger red blood cell and plasma yields. For example, initial fluid sample volumes that are applied may vary and have a minimum volume of about 10 microliters, and may range from about 10 microliters to about 100 microliters, about 10 microliters to about 75 microliters, and about 25 microliters to about 50 microliters.

Often plasma yields are low which makes detecting analytes more difficult. A low plasma yield would be less than about 4 µL. e.g., less than about 2 µL. However, the multilayer device described here may provide a plasma yield greater than about 2 µL, preferably ranging from about 4 µL to about 38 µL, including about 4 µL to about 15 µL, depending on the initially applied whole blood volume. There are several factors that may dictate the plasma yield, including the initial starting whole blood volume, the collection material, and loss of plasma due to spreading or leakage. Starting with a large initial whole blood volume results in the generation of a large plasma yield. The final plasma yield is also dependent on the collection material used for plasma collection—size and material type. If the collection material, preferably a cellulose or cellulose acetate paper, is thicker, a larger volume may be collected as there is more surface area. On average the plasma per whole blood of the multilayer device as tested here is about 0.303 f 0.007 µL plasma per µL whole blood. The multilayer device allows for greater than 0.100 µL plasma per µL whole blood. Whereas, the NOVIPLEX™ card results in 0.100 µL plasma per µL whole blood, which is significantly less than the amount achieved in the described multilayer device. Moreover, since each cutout may accommodate large volumes, i.e., about 10 microliters to about 100 microliters as necessary, the plasma yields per sample/cutout is sufficiently large to perform analysis. Other cards may require the combination of multiple fluid samples in order to achieve the same fluid sample volume of a single sample.

Moreover, in embodiments where the fluid sample is whole blood, the multilayer device is capable of processing a large and wide range of hematocrit levels. Hematocrit (Hct) is the proportion of red blood cells in a blood sample. For example, a 20 microliter blood sample having a 30% Hct has about 6 microliters of red blood cells, while a 45% Hct has about 9 microliters red blood cells, and a 60% Hct has about 12 microliters red blood cells with the remainder being plasma. Embodiments of the invention using a single or combination of two filtration membranes, preferably in one embodiment, asymmetric membranes, may provide a capacity to process blood samples having a hematocrit range of about 30% to about 70%. Although lower or higher hematocrit levels may work, they become problematic with regard to the membrane filtration process and would not be as efficient. Whole blood samples having a hematocrit range of about or greater than about 30%, about or greater than about 35%, about or greater than about 40%, about or greater than about 45%, about or greater than about 50%, about or greater than about 55%, about or greater than about 60%, about or greater than about 65%, about or less than 70%, about or less than about 65%, about or less than about 60%, about or less than about 55%, about or less than about 50%, about or less than about 45%, about or less than about 40%, about or less than about 35% are preferred. However, whole blood samples having hematocrit levels of about or greater than about 20% and about or less than about 80% may also be utilized but they are not as efficient.

One embodiment is directed to a multilayer device for use in collecting a fluid sample, e.g., whole blood, for testing analytes of interest, such as but not limited to, chemical compounds, drugs, drug metabolites, hormones, viruses, nucleic acids, DNA, RNA, mRNA, miRNA, proteins, cell surface and intracellular markers, and the like, or any analyte that is detectable by any known method or any of the means described here including, for example, spectroscopy or chromatography. Non-limiting examples of analytes may more specifically include opioids, cannabinoids, stimulants, performance enhancers, morphine, codeine, oxycodone, hydrocodone, amphetamine, methamphetamine, mephedrone, phentermine, 3,4-methylenedioxymethamphetamine (MDMA), fentanyl, combinations, and the like. Particularly in a sporting competition which requires drug testing to confirm that an athlete is not taking any performance enhancers, the methods and multilayer devices described here may be used to collect and separate fluid samples for testing any analytes of interest, including but not limited to foreign substances and endogenous biomarkers.

Another aspect of a multilayer device is its capacity to collect and analyze various components of a single fluid sample. Various analytes may be found in multiple locations of a single fluid sample, particularly if the fluid sample may be separated into its multiple components. In contrast to devices in the art, the novel multilayer device described here can advantageously process a single fluid sample, separate components of the single fluid sample, and individually analyze the separated components of the single fluid sample. This dual functionality is particularly beneficial for expediting testing of a large number of analytes and maximizing the use of a single fluid sample. A further advantage of the multilayer device is that any volume of fluid sample, for example, whole blood, may be applied to the multilayer device and still result in quantitative results since a filtration membrane unit comprises at least one pre-determined size which allows for a pre-defined volume. Combined with flow-through elution technology, quantitative analysis of the collected plasma on a collection material may be achieved. Alternatively, if flow-through elution technology is not used, the plasma spot may be punched out of the collection material and analyzed with the same spot size used when creating a calibration curve. Thus, accuracy of an applied sample volume is not a requirement as generally held in current technologies.

Another embodiment is directed to a multilayer device having dual function capacities where application of, for example, a whole blood sample from a single subject, results in a layer containing collected or retained cellular components, such as but not limited to, red blood cells, white blood cells, platelets, and other cells, and a layer containing collected or retained plasma. The cellular components may be analyzed separately from the plasma components in a sample, where each layer may contain different analytes found in differing components of whole blood. For example, cell surface proteins and other constituents on red blood cells as well as intracellular proteins and constituents and drugs contained within red blood cells may be analyzed separately from the plasma constituents. The dual function capability of the multilayer device of the invention is advantageous for its efficiency—sampling and time. Since the multilayer device can accommodate multiple samples and subsequently separate the multiple samples into their cellular component and their plasma component, multiple analytical tests may be simultaneously performed.

One advantage of a multilayer device having dual function capacities is that it facilitates the determination of a red blood cells to plasma partition coefficient of a drug or analyte of interest. Another advantage is the analysis of multiple classes of drugs or analytes performed simultaneously. Fluid samples from a single subject or multiple subjects may be simultaneously processed and analyzed for multiple analytes, i.e., each subject sample placed or collected in each cutout, well, or open hole of a multilayer device. For example, 4 opioids and 5 stimulants may be simultaneously tested for in a single process containing a single subject's fluid sample. The multiple layers of the inventive multilayer device enable the separation of, for example, blood components including red blood cells, plasma, platelets, and the like, as well as the processing of a wide range of hematocrit levels of a whole blood sample without hemolysis.

The multilayer device described here may in another embodiment be in the format of a book, which is hinged on one side and the various layers compose the pages of a book. Alternatively, the multilayer device may be coupled or attached at more than one side or edge, such as, for example, on all sides or edges of a multilayer device, and any or all layers may be detached or removed. The multilayer device of the invention may be in any shape, including but not limited to a circle, an oval, a triangle, a square, a rectangle, a parallelogram, a diamond, a pentagon, a hexagon, a heptagon, an octagon, and the like. Cutouts or holes of the multilayer device may be in any shape, including but not limited to a circle, an oval, a triangle, a square, a rectangle, a parallelogram, a diamond, a pentagon, a hexagon, a heptagon, an octagon, and the like as long as the cutouts or holes of the top cover and the hydrophobic membrane if utilized are the same. A preferred shape of the multilayer device is rectangular having four edges where the long edge forms at least one edge or side on which layers of the multilayer device may be hinged, coupled, or attached. The dimensions of the multilayer device in the shape of a rectangle may be about 1 inch to about 4 inches, preferably about 2 inches by about 3 inches, for example, about 2 inches by 3.3 inches. However, other shapes and sizes are also contemplated.

One embodiment is directed to a multilayer device or multilayer device card comprising:

a) a top unit, wherein said top unit comprises a filtration membrane unit adjacent to a hydrophobic membrane: and b) a bottom unit, wherein said bottom unit comprises a collection material, where said top unit is adjacent to and connected to said bottom unit, said filtration membrane unit comprising at least one filtration membrane, said filtration membrane unit has a top surface and a bottom surface, and said hydrophobic membrane has a top surface and a bottom surface, where said bottom surface of said filtration membrane unit is adjacent to said top surface of said hydrophobic membrane, where said collection material has a top surface and a bottom surface, and said bottom surface of said hydrophobic membrane is adjacent to said top surface of said collection material.

Another embodiment provides a multilayer device, comprising:

a) a top unit comprising layers of: a top cover with at least one cutout, a filtration membrane unit, and a hydrophobic membrane with at least one cutout: and b) a bottom unit comprising layers of: a collection material and a bottom cover without cutouts, where said top unit is adjacent to and connected to said bottom unit, said filtration membrane unit comprises at least one filtration membrane, preferably two filtration membranes of decreasing pore sizes with each having a shape of said cutout, said filtration membrane unit is positioned within said cutout of said top cover and adjacent to said hydrophobic membrane, said hydrophobic membrane is adjacent to or sandwiched between said filtration membrane unit and said collection material, said collection material is adjacent to said hydrophobic membrane, and said collection material is above said bottom cover. The filtration membrane unit in one embodiment may be sandwiched between the top cover and the hydrophobic membrane. The collection material in another aspect may be sandwiched between said hydrophobic membrane and said bottom cover. The multilayer device may be in the shape of rectangle having four edges, where each of the layers of the top unit or the bottom unit is temporarily coupled on at least one edge, and each of the layers of the top unit or the bottom unit is detachable or removable. In one embodiment, the filtration membrane unit may have the size and shape of the cutouts, fitting within each of the cutouts or wells of the top cover, such that each layer of the filtration membrane unit is held in place by the intimate contact of the edges of the filtration membrane unit and the walls of the cutout of the top cover and sandwiching of all of the layers in the multilayer device. A preferred embodiment is directed to these filtration membranes that are circular to fit within the circular cutouts of the top cover, where these circular filtration membranes or disks are easily removable for further analyses after collection and separation of samples. For example, after whole blood is applied to the cutouts of the multilayer device, the whole blood is allowed sufficient time to filter through the filtration membrane unit and collect on the collection material. Red blood cells remain on the filtration membranes or disks in one embodiment while plasma collects on the collection material.

An alternative format of a multilayer device further includes a contact support layer adjacent to and below said collection material and adjacent to or above said bottom cover, or in another embodiment, the contact support layer is combined with the bottom cover, such that the contact supports are a part of the bottom cover, and where contact supports of the contact support layer preferably contains raised supports where at least a portion of said raised supports fits within the cutout where a fluid sample is placed. A further embodiment comprises said multilayer device which may also include at least one window support for a layer detached for subsequent analyses, preferably for a filtration membrane unit and/or a collection material. The window support may be a layer containing a window which exposes the collected or captured sample for detecting an analyte of interest, said layer for subsequent analyses is attached or coupled to said window support, and said window support coupled to said layer for subsequent analyses may be removed or detached from said multilayer device for subsequent biological analyses. One embodiment comprises subsequent analysis of the filtration membrane unit, where each filtration membrane, or portions thereof, may be transferred for separate analyte detection analysis by, for example, enzyme immunoassay (EIA). Another embodiment comprises subsequent analysis of the collection material, where, for example, the plasma from a whole blood sample is analyzed by liquid chromatography and/or mass spectrometry, for example solid phase extraction liquid chromatography tandem mass spectrometry (SPE-LC-MS/MS).

An embodiment directed to a multilayer device comprises a top unit and a bottom unit, where the top unit and the bottom unit are adjacent. The top unit comprises a top cover, where the cover may be composed of a stiff, durable construction, such as for example card stock, an adjacent filtration membrane unit that initially comes in contact with a fluid sample of whole blood through a cutout or open hole of the top cover. An embodiment comprises a filtration membrane unit of at least one filtration membrane, and preferably two adjacent filtration membranes. Adjacent to and underneath the filtration membrane unit is a hydrophobic membrane. The bottom unit of the multilayer device comprises a collection material adjacent to a bottom cover. In one embodiment, the multilayer device may be in a format that allows for a top unit to be in constant or temporary contact with the underlying bottom unit. The top cover may have at least one cutout or open hole in which to place a sample, while the bottom cover does not have any cutouts. Multiple cutouts are preferred to test a fluid sample from a single source, for example, whole blood from a subject, and also to include standard controls for simultaneous testing.

Fluid Sample/Filtration Membrane

An embodiment may be directed to a fluid sample which is applied to a filtration membrane unit, where the filtration membrane unit is exposed through a cutout, well, or hole of a top cover of a multilayer device. The filtration membrane unit may comprise at least one filtration membrane, preferably two filtration membranes positioned adjacent to each other and within the confines of the cutout of the top cover. If the shape of a cutout or hole is circular, a preferred filtration membrane unit comprises at least one circular filtration membrane disk. The filtration membranes may be asymmetrical, non-asymmetrical, a combination of asymmetrical and non-asymmetrical, or similar combinations of each, i.e., one or more than one asymmetrical filtration membrane or one or more than one non-asymmetrical filtration membrane. The filtration membrane unit is selected and composed in a manner to sufficiently filter and capture components of a fluid sample. Preferably, for example, a multilayer device described here comprises a filtration membrane unit that separates components of a whole blood sample, where the filtration membrane unit captures red blood cells and allows plasma to flow or pass through the filtration membrane unit. If at least two filtration membranes are used, they are stacked such that there is an upper filtration membrane and a lower filtration membrane, and both filtration membranes have the same shape as the cutout or holes of the top cover and hydrophobic membrane if used.

The filtration membrane unit comprises at least one filtration membrane, which filters particles that are about 1 micron to about 10 microns, about 2 microns to about 5 microns. A filtration membrane has a top or first surface and a bottom or second surface and a thickness sufficient to allow filtration and/or capture of desired particles, such as for example, red blood cells from a whole blood sample, and allowing other particles or fluids to filter through, for example plasma. The filtration membrane may have a thickness ranging from about 0.1 mm to about 0.6 mm, about or greater than about 0.15 mm, about or greater than or less than about 0.2 mm, about or greater than or less than about 0.26 mm, about or greater than or less than about 0.3 mm. However, if the thickness exceeds these values, blockage or plugging of the filtration membrane may likely occur, thus inhibiting filtration. Another embodiment is directed to a filtration membrane unit comprising two adjacent filtration membranes. When two adjacent filtration membranes are utilized, a bottom surface of a first filtration membrane is adjacent to a top surface of a second filtration membrane, where a sample enters a top surface of a first filtration membrane and exits through a bottom surface of the first filtration membrane and enters a top surface of a second filtration membrane and exits a bottom surface of the second filtration membrane.

A filtration membrane may be hydrophobic to avoid absorption of any plasma, but may also be hydrophilic in other circumstances, and anisotropic, functioning to filter and collect desired components of a fluid sample. For example, the desired components of a whole blood sample may include, but are not limited to, red blood cells and plasma. The filtration membrane may comprise any material sufficient to filter and separate particles of interest. In an embodiment, the filtration membrane, which allows filtration of whole blood components, may be composed of, but not limited to a polar, non-polar, and intermediate polarity polymers, polyester, polysulfones, polycarbonate, polymethacrylate, or the like, or blends or combinations thereof.

The filtration membrane functions to filter and separate components of a fluid sample. When the fluid is whole blood, the sample may be separated into individual components, i.e., red blood cells, white blood cells, platelets, and plasma, and collect, for example red blood cells for further testing, while allowing other components, such as plasma to filter through the membrane. It is known in the art that red blood cells are larger in size than plasma or platelets, where red blood cells may be about 6 micrometers (µm)—about 8 µm, and white blood cells are larger than red blood cells, i.e., about 12 µm-about 15 µm. Appropriate filtration membrane pore sizes may be selected depending on the desired particle. A filtration membrane closest or adjacent to a hydrophobic membrane may have characteristics sufficient to collect or capture components of whole blood, for example, red blood cells. One advantage of the subject multilayer device is its novel capability to separate, collect, and test more than one blood component of a single subject sample or multiple subject samples of whole blood for separate analyses, where the device accommodates a large volume of and wide hematocrit percentage range of whole blood sample.

Another embodiment is directed to filtration membranes that are asymmetric allowing for the whole blood sample to be filtered, separating different sized components within the filtration membrane unit. For example, the filtration membrane unit and its filtration membranes allow for separating and capturing red blood cells from a whole blood sample and permitting plasma to flow through the filtration membrane unit and results in cell-free plasma. An asymmetrical filtration membrane may be used in one embodiment of a multilayer device. The asymmetrical filtration membrane has a top surface that allows particles of a large size and smaller to enter the membrane, w % bile the bottom surface of the same filtration membrane has a smaller pore size, thereby eliminating any particles smaller than the top surface pore size and greater than the pore size at the bottom surface of the filtration membrane from filtering or passing through, i.e., capturing some particles or allowing particles smaller than the pore size on the bottom surface of the filtration membrane to pass. Another embodiment may be directed to a filtration membrane unit comprising at least one asymmetrical filtration membrane or at least two asymmetrical filtration membranes, where the asymmetrical filtration membrane may have a pore size of about 5 microns at the top surface, and a pore size at the bottom surface of about 2.5 microns, thereby collecting particles that are smaller than about 5 microns and larger than about 2.5 microns in a filtration membrane and gradually allowing or filtering particles that are smaller than about 2.5 microns. Another embodiment is directed to sequential filtration utilizing two filtration membranes in a filtration membrane unit. A portion of red blood cells and any particles that are larger than 5 microns may be captured on a top or first filtration membrane and then the remaining red blood cells and any particles that are larger than 2.5 microns and smaller than 5 microns may be captured on a bottom or second filtration membrane.

Optimal performance of a lower filtration membrane might occur with a pore size of about one (1) micron. Filtration membrane pore sizes may range from about 1 micron to about 10 microns in a multilayer device of the invention. In one example, an upper, top filtration membrane may have a pore size of about 10 microns thereby providing preliminary filtration of larger particles and mitigating obstruction of the lower filtration membrane, which may have a pore size of about 1 micron.

A filtration membrane unit comprising either a single filtration membrane or a dual layered filtration membrane comprising two filtration membranes of a multilayer device may process a wide variety of fluid samples. When two filtration membranes are used in a filtration membrane unit, a first filtration membrane adjacent to a top cover and a second filtration membrane, where the first uppermost filtration membrane may have a pore size ranging from about 35 microns to about 3 microns, about 5 microns, while the second, lower filtration membrane adjacent to or sandwiched by a first filtration membrane and a hydrophobic membrane may have a pore size that is generally smaller than that of the first filtration membrane. A preferred pore size range for the second filtration membrane may be 3 microns to about 0.2 microns, about 2.5 microns. In a two filtration membrane or dual layered filtration membrane embodiment, the filtration membrane may each be asymmetrical or non-asymmetrical, or alternatively, one filtration membrane is asymmetrical and the other is non-asymmetrical.

One embodiment comprises a multilayer device composed of a filtration membrane unit that is an asymmetric membrane. Another embodiment is directed to a multilayer device having a top unit, where the filtration membrane unit is composed of two filtration membranes. In one embodiment, the top or uppermost filtration membrane layer is a commercially available product iPOC$^{DX}$™ X asymmetrical 5 mm membrane that has a 35 µm top and a 5 µm bottom (International Point of Care Inc.; Toronto, Canada), or a filtration membrane with similar properties or properties sufficient to filter desired components. Yet another embodiment is directed to a bottom or lowermost filtration membrane that is a commercially available product iPOC$^{DX}$™ S/G asymmetrical 7 mm membrane that has a 35 µm top and a 2.5 µm bottom (International Point of Care Inc.; Toronto. Canada), or a filtration membrane with similar properties or properties sufficient to filter desired components.

Hydrophobic Membrane Layer

Adjacent to or beneath a filtration membrane unit or sandwiched between a filtration membrane unit and a collection material layer, is in one embodiment, a hydrophobic membrane layer, which assists with the complete and direct contact of a sample with the various membrane layers and accomplishment of sample spot uniformity. Although the multilayer device may be successful in separating and collecting various whole blood components without this hydrophobic membrane, particularly in those multilayer devices that have an intimate seal or connection between the layers, its inclusion results in superior outcomes. Alternatively, the hydrophobic membrane may be positioned above and adjacent to the collection material. For example, without the hydrophobic membrane in those embodiments that utilize a paper or cardboard type cover which may lack a tight or intimate closure, instead of a circular spot, filtration may result in a horseshoe-shaped spot on a collection material, which is not ideal for the preferred subsequent automated spectroscopic analyses. The hydrophobic membrane may be a layer the same size, shape, and dimensions as the entire multilayer device and contain cutouts or holes in the same size, shape, and dimensions as the cutouts in the top cover. The hydrophobic membrane may be composed of any material that is hydrophobic, preferably polyester, polyester blends, polysulfone, or polycarbonate, and the like. The hydrophobic membrane layer may be any material or membrane that is sufficient to aid in the placement and containment of the individual layers to avoid movement or displacement, as well as, to assist in sample spot uniformity. In one embodiment, the hydrophobic membrane underneath and adjacent to the filtration membrane unit that filters a whole blood component, such as for example, red blood cells, may preferably be composed of a polyester or a polyester blend, more preferably, Ahlstrom HOLLYTEX® Grade 3256 nonwoven polyester (Ahlstrom Filtration; Mount Holly Springs, PA) which has a thickness of about 0.058 millimeter and a basis weight of about 23.9 g/m.

Collection Material Layer

Another layer of a useful multilayer device which is located underneath a hydrophobic membrane layer is a collection material layer that acts as a vessel for collecting filtered desired components from a small volume of initially applied fluid sample. After drying the collected sample, a dried spot formed on the collection material allows for a convenient storage means for future quantitative analyses. Other components of whole blood are separated from plasma in the preceding or layers above the collection material. The collection material functions to absorb and/or collect plasma retrieved from filtration of a whole blood sample. The collection material has features that allow the capture and collection of plasma, such as for example a pore size preferably in a range of about 35 microns to about 0.2 microns and a thickness of about 0.1 millimeter to about 0.6 millimeter, preferably about 0.19 mm. The pore size may be a factor that expresses the degree of absorptivity. In a preferred embodiment, the collection material may be composed of cellulose, paper cellulose made from cotton linter pulp, and may also be a material of but not limited to cellulose acetate, or the material used in WHATMAN 903 (WHATMAN®, Springfield Mill, United Kingdom), AHLSTROM® 226 (AHLSTROM® Corporation, Helsinki, Finland), etc. A preferred collection material for use in a multilayer device is AHLSTROM® 601 cellulose paper (Ahlstrom Filtration; Mount Holly Springs, PA); however, any material capable of separating and collecting, for example, plasma from a whole blood sample or having similar properties as cellulose paper may also be used. Cellulose paper as a collection material is preferred for its capacity to concentrate the spots within the cutout area, contribution to avoiding undesired chemicals in a collected sample (e.g., the Center for Disease Control and Prevention (CDC) tests and confirms the purity of such cellulose papers used for dried spot cards), and its stabilization properties of drugs or analytes of interest found in a collected sample. Collection material layers that dilute sample spots, are fragile, and have unknown stabilization properties are not ideal or useful for the invention. In a dried stage of a sample, enzymatic decomposition of drugs and other chemical substances is minimized. However, the drug or other chemical analytes may still decompose due to oxidation. In some instances, chemical entities, such as for example, cannabinoids are unstable when exposed to air and moisture, so there is a need in the art of whole blood sample collection and testing to ensure stability. Typically an inert atmosphere (i.e., removal of oxygen) or the use of a silica gel drying agent may be used. For purposes of the described multilayer device and uses thereof, an inert atmosphere, such as but not limited to, nitrogen or argon gas maintained in a leak-proof container, is not necessary during sample collection but may be used. The stability of the analytes on the multilayer device is sufficient during sample collection in the absence of an inert atmosphere. The presence of drying agent or inert atmosphere may be beneficial during sample transport after the sample has dried and storage including long term storage of months or years. A drying agent packaged with the multilayer device containing a sample does not affect the results of testing for analytes of interest. However, for long-term maintenance or storage, an additional storage device that is filled with an inert gas, e.g., nitrogen gas, may be used to store the multilayer devices, in particular the filtration membrane unit and collection material layer, thereby providing chemical stability of the analytes in the dried spot samples. While specific analytes may require an inert atmosphere or drying agent during sample collection and/or storage, generally they are not necessary and preferred especially in most field settings when collecting samples.

Supportive Layer

Other layers of a multilayer device described here may include those that support the multilayer device. The covers or support covers of such a multilayer device which sandwiches the top unit and bottom unit may be made of a stiff, durable construction, such as but not limited to, for example, card stock, polymers, plastics, nylons, polyamides, Acrylonitrile Butadiene Styrene (ABS), Polylactic Acid (PLA), Polyvinyl Alcohol (PVA), and the like. Specifically, certain layers of a 3D-printed multilayer device may be manufactured using polymers, plastics, nylons, polyamides. Acrylonitrile Butadiene Styrene (ABS), Polylactic Acid (PLA), Polyvinyl Alcohol (PVA), and the like. The supportive cover may be composed of an upper or top cover and a lower or bottom cover, where the upper cover is the topmost layer that is adjacent to or above a filtration membrane layer, and where the bottom cover is the bottommost layer that is underneath a collection material layer or in some embodiments a contact support layer. The top cover preferably has at least one cutout such that a filtration membrane unit is exposed. Another embodiment is directed to a multilayer device comprising a top cover containing at least two cutouts exposing a filtration membrane unit. A preferred embodiment is directed to a top cover with four cutouts exposing a filtration membrane unit. However, the number of cutouts may be determined by the size and dimensions of the multilayer device and the number of cutouts that may be accommodated on the top cover. The top cover may have at least one cutout, at least two cutouts, at least three cutouts, and preferably at least four cutouts. In contrast, the bottom cover does not contain any cutouts. Rather, the bottom cover is a solid construction to provide support for all of the above preceding layers on top of the bottom cover.

The top cover may have cutouts such that the filtration membrane unit layer is directly exposed. A fluid sample when applied to a filtration membrane unit of a multilayer device forms a spot that is inside or within the perimeter of the top cover cutout. The filtration membrane unit is a layer that has dimensions that are the same as or about the same size as the cutout, may extend beyond the perimeter of the top cover cutout, or is the same as the perimeter of the entire cover support layer and multilayer device as a whole. For example, a multilayer device may have a top cover with circular cutouts each having a diameter of, for example, about 5 mm and a filtration membrane unit in a similar circular shape, e.g., a disk, with a diameter that is the same as that of the top cover, i.e., about 5 mm such that the filtration membrane unit fits within the perimeter and area of the top cover cutout. Alternatively, the filtration membrane unit is a layer having dimensions that extend beyond the perimeter of the top cover cutout and to the perimeter edges of the cover. Another embodiment is directed to a filtration membrane unit comprising at least one filtration membrane layer that is in the shape of a round disk, i.e., the shape of a cutout which fits within the cutout of the top cover. Should the multilayer device be in the shape of a rectangle with dimensions of about 2 inches by about 3 inches, a filtration membrane unit layer, in another embodiment, may have the same shape and dimensions, where the top cover cutout exposes a portion of the filtration membrane unit. In one embodiment, an outline of the cutout may be delineated on one or more layers of the multilayer device, such as for example, any or all layers of the filtration membrane unit, the hydrophobic membrane, and the collection material.

The covers and intervening layers are preferably coupled on one side similar to the spine of a book, where each intervening layer is removably detachable. Alternatively, all of the edges of the covers are coupled, or temporarily coupled in a closed position formation. For example, any or all of the edges may be perforated to allow separation and removal of any of the layers. When all of the layers of the multilayer device are coupled and the top unit and bottom unit are closed and in contact, a stable book-type card may be used for sample collection.

One embodiment of the multilayer device is directed to a rectangular-shaped book-type card for processing a whole blood fluid sample, separating blood components, and detecting analytes. The layers of the product comprise a top cover and a bottom cover sandwiching the intervening layers, where the top cover has four cutouts, wells, or open holes, and the top and bottom support covers are connected or hinged on at least one side or edge of the multilayer device. Underneath and adjacent to the top cover is a filtration membrane unit comprising a first filtration membrane and second filtration membrane. Wherever there are cutouts in the top cover, a first filtration membrane of a filtration membrane unit is exposed. Otherwise, the top cover covers the first filtration membrane and underlying layers. Another filtration membrane or second filtration membrane is adjacent to and underneath the first or topmost filtration membrane, such that a fluid sample flows from the top surface of the first or topmost filtration membrane down and through the bottom surface of a second filtration membrane of the filtration membrane unit. Underneath and adjacent to the filtration membrane unit is a hydrophobic membrane layer which also has the same dimensions as the support covers. The filtration membrane unit and underlying hydrophobic membrane may be temporarily coupled together to the top cover forming a top unit. Such a formation allows all of the underlying layers of the filtration membrane unit and hydrophobic membrane to be simultaneously lifted together when the top cover is lifted. Any or all of the layers may be removed from the book-type multilayer device for subsequent analyses. For example, the filtration membrane unit and collection material layers may be temporarily attached or perforated on at least one edge or side and removed or torn at the perforation, thereby separating the layers for subsequent analyses.

Adjacent to and underneath the hydrophobic membrane layer in the book-type multilayer device card is a collection material layer which may lack or preferably has an outline depicting the circular cutout from the top cover such that the user may observe where a sample was initially placed and contains plasma retrieved from a whole blood sample.

Another embodiment may include a window support layer for automated analyses, preferably an online-amenable window support layer, which is coupled to the collection material, such that the window support layer has an opening or window that exposes the collection material, particularly the outlined circular cutouts where plasma separated from the whole blood fluid sample has spotted. The collection material may have dimensions smaller than the covers or the same dimensions as the covers. The window support may have an identifiable mark, such as but not limited to, a barcode including a QR code or Quick Response code which contains a sample number, a sample patient or subject identifier or name, or any other information for identifying the sample, as well as any other information including but not limited to time tracking, document management, URL (uniform resource locator). GPS (global positioning system), etc.

The window support layer, preferably online-amenable window support layer, with an opening or window may, in one embodiment, be located underneath or adjacent to the hydrophobic membrane layer. A collection material may have a border that is affixed or coupled to the underside of the online-amenable window layer such that the outlined circles where filtered sample spots of the collection material are exposed through the window opening of the online-amenable window support layer. A non-leaking surface region may be achieved by affixing a perimeter of the collection material to the underside of the window layer where the collection material perimeter makes an intimate, non-leaking physical contact extending beyond the window opening. The online-amenable window layer coupled to the collection material may be removed together from the multilayer device by at least one perforated edge, which also forms the spine of the book-type multilayer device. The online-amenable window layer with collection material may be removed from the multilayer device by tearing at the perforation without affecting the contents of the collection material. Alternatively, the online-amenable window layer comprises two layers sandwiching the collection material, where the outlined circular cutouts of the collection material are exposed through a window on each of the two layers of the online-amenable window layer. The collective two-layered online-amenable window layer sandwiching the collection material may be removed or detached from the multilayer device for further analyses, particularly of analytes of interest.

Another support layer that may be used in a multilayer device is a contact support layer containing the same number of cutouts as found throughout the multilayer device construction. This contact support layer is raised to aid in a fluid sample making contact to all layers of the multilayer device. Even without this support layer, the filtration and separation of whole blood components can be achieved. However, the inclusion of this raised support layer ensures a physical contact of the filtration membrane, hydrophobic membrane, and collection material layers thereby contributing to the superior formation of a uniform sample spot and collected yield. When the top unit and the bottom unit of a multilayer device are in contact in a closed formation, the raised contact support layer assisted with complete filtration via physical contact of the layers. In another embodiment, a contact support layer that ensures a physical contact between the filtration membrane unit and collection material may be adjacent to or underneath the collection material portion within the window or windows of the window support layer. This contact support layer may contain raised disks made of, for example, card stock, plastics, or any relatively rigid or similar material, where the top layer cutouts are located and also in line with the outlined circular cutouts of the collection material. The raised contact support may comprise a disk or raised platform of different sizes, where one may be the size of a cutout and an underlying platform may be slightly larger in diameter than the cutout size. An alternative formation may include an entire support layer having the same dimensions as the top and bottom covers, such that the raised portion of the support layer is aligned with the circular sample cutout locations and the remaining areas of the support layer are not raised and extend to the dimensions of the top and bottom covers. Another embodiment encompasses a bottom cover containing contact supports, thereby providing a dual function for the bottom cover.

A further embodiment encompasses all of the features as described in the subject multilayer device and additionally includes another window support layer coupled or adjacent to a filtration membrane containing a different component of a whole blood sample. The collective window support layer and filtration membrane when removed or detached from the multilayer device allows subsequent analyses for analytes of interest similarly to the collective window support layer and collection material.

In this book-type multilayer device card embodiment, a bottom unit may comprise a window support layer, collection material, contact support layer, and a back cover, where all of the layers are temporarily coupled or removably coupled on at least one of the same edges or sides of the book-type multilayer device. The collective bottom unit may come into contact with the top unit when desired, or may be separated in a manner to allow the detachment or removal of any or all layers of the multilayer device.

Another embodiment may be directed to a multilayer device, comprising:
  a) a top unit, wherein said top unit comprises a filtration membrane unit; and
  b) a bottom unit, wherein said bottom unit comprises at least one collection material,
where said top unit is connected, coupled, or secured to said bottom unit, said filtration membrane unit comprising at least one filtration membrane, said filtration membrane unit has a top surface and a bottom surface, where said collection material has a top surface and a bottom surface, and said bottom surface of said filtration membrane unit is adjacent to or above said top surface of said collection material. The top unit may optionally contain a hydrophobic membrane beneath or adjacent to the filtration membrane unit and above or adjacent to the collection material. This multilayer device may be produced using cardstock or any other sturdy construction or alternatively by additive manufacturing, or 3D printing.

Another embodiment provides a multilayer device, comprising:
  a) a top unit comprising layers of: a top cover with at least one cutout or hole and a filtration membrane unit within each cutout; and
  b) a bottom unit comprising layers of: a collection material and a bottom cover,
where said top unit is connected, coupled, or secured to said bottom unit, said filtration membrane unit comprises at least one filtration membrane, preferably two filtration membranes of decreasing pore sizes with each having a shape of said cutout or hole. At least one cutout or hole may be in any shape, including but not limited to a circle, an oval, a triangle, a square, a rectangle, a parallelogram, a diamond, a pentagon, a hexagon, a heptagon, an octagon, and the like as long as the cutouts or holes of the top cover and the hydrophobic membrane, if utilized, are the same, said filtration membrane unit is, preferably, positioned within said cutout or hole of said top cover and adjacent to said bottom unit, said filtration membrane unit is adjacent to said collection material, and said collection material is above and adjacent to said bottom cover. The filtration membrane unit in one embodiment may be sandwiched between the top cover and the bottom unit. Alternatively, the filtration membrane may have a different shape than the cutouts or holes of the top cover and/or the hydrophobic membrane. For example, in one embodiment, the holes or cutouts of the top cover are circular: whereas, the filtration membrane unit underneath the holes or cutouts of the top cover is rectangular sufficiently sized to span beneath the at least one hole or cutout, and preferably spanning beneath all of the holes or cutouts of the top cover. However, in this embodiment, the rectangular filtration membrane unit has a boundary or border to centralize the sample spots after application of a fluid sample to the cutouts or holes of the top cover and to prevent the filtration membrane unit from absorbing plasma. Inclusion of the filtration membrane unit containing a border or boundary may allow for the elimination of a hydrophobic membrane, but may optionally still be used for increased effectiveness. If a hydrophobic membrane is utilized, it has as many cutouts or holes as presented in the top cover, and in the same shape and sizes of the cutouts or holes in the top cover. If the hydrophobic membrane is used, it is preferably beneath and adjacent to the collection material; however, in another embodiment, the hydrophobic membrane may be above and adjacent to the collection material. The collection material in another aspect may be sandwiched between said top unit and said bottom cover. The multilayer device may be in the shape of rectangle having four edges, where each of the layers of the top unit or the bottom unit is temporarily coupled on at least one edge, preferably at least two edges, and more preferably at least four edges, and each of the layers of the top unit and the bottom unit is detachable or removable. This multilayer device may be produced by 3D printing.

Another embodiment comprises a 3D-printed multilayer device for separating blood components, comprising:
  a top unit comprising layers of: a top cover with four (4) cutouts and at least one filtration membrane in the form of a disk fitting within each of the four cutouts: and
  a bottom unit comprising layers of: a collection material affixed to a window support, and a bottom cover with contact supports,
where said top unit is adjacent to and intimately coupled or connected to said bottom unit, sandwiching intermediate layers of the multilayer device described here, where each filtration membrane sufficient to separate blood components is positioned within each of said cutouts of said top cover and adjacent to said bottom unit, each disk of said filtration membrane is adjacent to said collection material, and said collection material is above and adjacent to said bottom cover containing raised contact supports. The filtration membrane in one embodiment may be sandwiched between the top cover and the bottom unit. The collection material may be sandwiched between said top unit and said bottom cover with contact supports. The multilayer device may be in the shape of a rectangle having four edges, where each of the layers of the top unit and the bottom unit is temporarily coupled on at least two edges of the multilayer device, and each of the layers of the top unit and the bottom unit is intimately contacted with its adjacent layers, and each of the layers is detachable or removable.

One embodiment may be directed to the application of about 20 microliters of whole blood to a filtration membrane disk (~9 mm thickness) within each cutout of a multilayer device and incubated at room temperature for about 3 minutes. Once the separated blood components have dried, the multilayer device is disassembled removing the filtration membrane layer and collection material layer. The filtration membrane disk or disks are subjected to cellular analysis of the red blood cells collected thereon, and the dried plasma spots on the collection material are subjected to chemical analyses.

In one embodiment, the multilayer device comprises a 3D-printed top cover, bottom cover comprising contact supports, and a window support through which the contact supports may be in physical contact with a collection material layer which covers the open window. The top cover comprises at least one cutout, preferably 4 cutouts, in which a filtration membrane unit is placed, and the filtration membrane unit contains at least one filtration membrane disk, preferably two asymmetrical filtration membrane disks which fit within the cutouts of the top cover. Where two asymmetrical filtration membrane disks are stacked to form a filtration membrane unit, one filtration membrane disk is on top of the other filtration membrane disk forming a filtration membrane unit comprising an upper filtration membrane disk and a lower filtration membrane disk, where each filtration membrane disk has a top surface and a bottom surface, where a fluid sample is initially in contact with the top surface of the upper filtration membrane disk and bottom surface of a lower filtration membrane disk is adjacent to a collection material layer, while the filtration membrane unit is within the perimeter of the hydrophobic membrane sandwiched between the top cover and the collection material. An alternative embodiment contemplates a filtration membrane unit layer, i.e., not in disk form, where the filtration membrane unit layer contains a border or boundary to centralize the sample spot and prevent the filtration membrane unit from absorbing plasma thereby eliminating the need for a hydrophobic membrane. Preferably, the bottom surface of a filtration membrane unit, comprising two filtration membrane disks, may be fluidly connected to a collection material layer which is attached or affixed to a window support, where the collection material covers an open window of the window support. The window support may extend beyond the collection material layer to the edges of the top cover layer. Through the window of the window support, contact supports of a bottom cover is placed in contact with the collection material layer.

A 3D-printed multilayer device, comprising:
(a) a top unit comprising layers of: a top cover with at least one hole, preferably four (4) holes: a filtration membrane unit; and a hydrophobic membrane with at least one hole, preferably four (4) holes, wherein the number of holes of said top cover is the same as the number of holes of said hydrophobic membrane; and
(b) a bottom unit comprising layers of: a collection material; a window support, and a bottom cover with raised contact supports, wherein said top unit is connected or intimately coupled to said bottom unit, sandwiching intermediate layers of the multilayer device, wherein said filtration membrane unit comprises two filtration membrane disks, wherein said filtration membrane unit comprises an upper filtration membrane disk and a lower filtration membrane disk, wherein each filtration membrane disk contains a top surface and a bottom surface, said bottom surface of said upper filtration membrane disk is adjacent to said top surface of said lower filtration membrane disk, wherein said filtration membrane unit separates or sufficiently separates blood components and is concentrically positioned within the perimeter of each of the four holes of said top cover and said filtration membrane unit is concentrically positioned within the perimeter of each of the four holes of said hydrophobic membrane; said hydrophobic membrane is adjacent to said top cover and said hydrophobic membrane is adjacent to said collection material, and said collection material is adjacent to said raised contact supports of said bottom cover. The multilayer device comprises 3D-printed layers of: a top cover, a window support, and a bottom cover.

In another embodiment, a multilayer device may comprise 3D-printed layers of a top cover and a bottom cover, where said top cover comprises at least one hole, preferably four holes, where a filtration membrane unit comprising at least one filtration membrane disk, preferably two filtration membrane disks, wherein said filtration membrane unit comprises an upper filtration membrane disk and a lower filtration membrane disk, wherein each filtration membrane disk contains a top surface and a bottom surface, said bottom surface of said upper filtration membrane disk is adjacent to said top surface of said lower filtration membrane disk, wherein said filtration membrane unit is concentrically positioned within the perimeter of each of the four holes of said top cover, and said bottom cover comprises a trough or well with a lip to secure a collection material or alternatively secure a hydrophobic membrane and said collection material, where said hydrophobic membrane is adjacent to said top cover and to said collection material, wherein said trough or well contains raised contact supports positioned in alignment with said holes of said top cover and if present, said raised contact supports are positioned in alignment with said holes of said hydrophobic membrane, said hydrophobic membrane is adjacent to said top cover and said hydrophobic membrane is adjacent to said collection material, and said collection material, and said hydrophobic membrane if present, is secured within said trough or well such that the filtration membrane unit and collection material are fluidly connected, and said top cover is coupled, affixed, or secured to said bottom cover.

The filtration membrane unit preferably comprises at least one filtration membrane in the form of a disk which is pre-formed and contains a pre-defined volume of a sample. Quantitative analysis of a collection material layer can be accomplished by using a system that utilizes flow-through elution of whole blood plasma components on a collection material layer coupled with mass spectrometry, or alternatively, punching a portion of a collection material containing plasma. As long as a punched sample spot size is the same size as those used in calibration curve samples, the spot size of a collection material layer is not of concern since a pre-defined volume of a fluid sample was applied to the filtration membrane unit, i.e., filtration membrane pre-formed disk. This is particularly advantageous when finger-pricked whole blood is applied to the multilayer device without using a volumetric control device such as for example, a volumetric pipette or micropipette. Since typically there can be a variation in volume of a fluid sample in the absence of such volumetric control, plasma spot sizes generated from differing volumes of blood may be analyzed by punching out a pre-determined spot size of a collection material for analysis and applying the same spot size for calibration samples. So either the flow-through elution of dried plasma spots or same sized sample and calibration spots are used for techniques other than flow-through elution for subsequent analysis.

If an entire plasma spot instead of a sub-spot is to be used for analysis, quantitative analysis can also be achieved under two conditions—using a volumetric control device such as a pipette to apply a known volume of whole blood sample and adjusting the hematocrit level of the whole blood sample. These conditions allow for a fixed size plasma spot. Therefore, an entire plasma spot can be used for quantitative analysis.

A 3D-printed multilayer device, comprising:

(a) a top unit comprising layers of: a top cover with at least one hole, preferably four (4) holes, and a filtration membrane unit comprising at least one filtration membrane disk, preferably two filtration membrane disks, and said filtration membrane unit positioned within each of the holes of said top cover: and (b) a bottom unit comprising layers of: a collection material and a bottom cover with raised contact supports, wherein said top unit is adjacent to and intimately coupled or connected to said bottom unit, sandwiching intermediate layers of the multilayer device, wherein said filtration membrane unit comprising two filtration membrane disks comprises an upper filtration membrane disk and a lower filtration membrane disk wherein each filtration membrane disk contains a top surface and a bottom surface, said bottom surface of said upper filtration membrane disk is adjacent to said top surface of said lower filtration membrane disk, wherein said filtration membrane unit is concentrically positioned within the perimeter of each of the holes of said top cover and said filtration membrane unit is concentrically positioned above each raised contact support, said collection material is adjacent to said collection material, said bottom cover is positioned within each of said cutouts of said top cover, said filtration membrane unit is adjacent to said collection material, and said collection material is secured and adjacent to said bottom cover containing raised contact supports.

This 3D-printed multilayer device may be disposed of to avoid contamination between samples, or alternatively, carefully sanitized and decontaminated for multiple uses with new or unused filtration membrane disks and collection materials. A preferred embodiment is directed to a 3D-printed multilayer device that is manufactured using any one of a variety of methods that result in a multilayer device described here that secures or tamper-proofs the collected samples.

Methods/Uses of the Multilayer Device

A further embodiment may be directed to the use of or a method of using a multilayer device for the analyses of a fluid sample for analytes of interest. A method comprises applying a biological fluid sample, such as for example, whole blood, to the top surface of a filtration membrane unit, filtering the sample by allowing an amount of time sufficient for the fluid sample to pass through the filtration membrane unit and collect on the collection material, separating the filtration membrane unit from the collection material such that, for example, red blood cells are captured or collected on the filtration membrane unit and plasma is captured or collected on the collection material, and analyzing the separated and collected samples for desired target analytes, manually or in another embodiment by automated means. For example, the analysis may be automated and online, where the target analytes are analyzed by liquid chromatography (LC), mass spectrometry (MS), LC/MS, LC/MS/MS, and the like. Prior to analyses, in one embodiment, the analytes may be extracted by direct elution and solid phase extraction (SPE). The fluid sample may be a small volume, less than about 70 µl, about or less than about 50 µl, about or less than about 25 µl, and the like. The advantage of this method is that it may be performed without centrifugation and is a quick and accurate method.

Another embodiment is directed to a method of using a multilayer device comprising:

a) applying a flexible volume of a fluid, such as a volume of whole blood to a multilayer device comprising: (i) a top unit comprising layers of: a top cover with at least one cutout or open hole on or in which a fluid sample is placed, a filtration membrane unit, and a hydrophobic membrane; and (ii) a bottom unit comprising layers of a collection material and a bottom cover without cutouts or open holes, where the filtration membrane unit is exposed through the cutout of the top cover of the multilayer device, where the top unit is adjacent to said bottom unit, where the top and bottom units may be closed in physical contact, where the fluid sample has a flexible volume ranging from about 10 microliters to about 50 microliters, where the multilayer device comprises at least one filtration membrane, a hydrophobic membrane, and a collection material;

b) after application of the fluid sample, waiting for about 3 minutes or a period of time sufficient to filter the fluid sample, where the top unit is in contact with the bottom unit in a closed formation;

c) separating or removing the filtration membrane unit layer and/or the collection material layer from the multilayer device, where the filtration membrane unit and the collection material each contain different components of the fluid sample:

d) waiting for about 30 minutes, or until the components of the fluid sample on the filtration membrane unit and the collection material are sufficiently dried; and e) analyzing the filtration membrane unit and/or the collection material containing dried fluid sample components for analytes of interest.

Another embodiment is directed to method of using a multilayer device, comprising:

a) applying a volume of whole blood to said filtration membrane unit of said multilayer device:

b) waiting for an amount of time sufficient for separation of blood components of said whole blood; and c) storing said multilayer device, and optionally transporting the multilayer device for analysis.

For example, an athlete who needs to be tested for doping may obtain a multilayer device described here, and after applying a volume of whole blood using a finger prick technique to each of the cutouts and waiting for an amount of time sufficient for separation of blood components of the whole blood sample or for the blood components to dry, the athlete would appropriately store the multilayer device and return or send the multilayer device to an on-site or separate facility to perform analyses to determine if the athlete was clean, i.e., the whole blood sample was absent any unauthorized drug or biological component or doping, i.e., the whole blood sample had an unauthorized drug or biological component present.

Once a facility receives a multilayer device with a sample contained thereon, the method further comprises:

d) separating said filtration membrane unit and said collection material from said multilayer device, where the sample has been separated and dried; and e) analyzing said filtration membrane unit and/or said collection material containing the sample. An internal standard, positive control, and negative control may also be utilized in accordance with the test.

After a whole blood sample has been collected, separated, and dried in the multilayer device described here, the filtration membrane unit and collection material may be separated from the multilayer device for separate analyses using techniques commonly used and known in the art. Some of these techniques include but are not limited to liquid chromatography-tandem mass spectrometry (LC/MS/MS), high performance liquid chromatography (HPLC) with UV detection, liquid chromatography-high resolution mass spectrometry (LC-HRMS), liquid chromatography-time-of-flight/mass spectrometry (LC-TOF/MS), ultra-performance liquid chromatography-tandem mass spectrometry (UPLC-MS/MS), HPLC-Diode Array Detection (HPLC-DAD), Gas chromatography-negative-ion chemical ionization mass spectrometry (GC-NICI-MS). HPLC fluorescence detector with enhanced sensitivity (HPLC-FLU), LC/MS, electrospray ionization-TOF (ESI/TOF), matrix-assisted laser desorption/ionization-TOF (MALDI/TOF), Quadrupole time-of-flight (QTOF), Ion Trap, OrbiTrap, Inductively Coupled PlasmawMS, and the like.

The multilayer device may be in an opened or closed formation at the time a fluid sample or whole blood sample is applied to the filtration membrane unit through the at least one cutout of the top cover. A multilayer device in a closed formation occurs when a top unit comprising a top cover, a filtration membrane unit, and a hydrophobic membrane, and a bottom unit comprising layers of a collection material, optionally a window support, optionally a contact support, and a bottom cover are in contact via the hydrophobic membrane and the collection material. An opened formation may be one where the top unit and the bottom unit are not in contact, i.e., the hydrophobic membrane of the top unit and the collection material of the bottom unit are separated or lacking contact. One embodiment is directed to a multilayer device that is in the closed formation when a volume of fluid sample is applied. Another embodiment is directed to a multilayer device that is initially in the opened formation when a volume of fluid sample is applied and then closed beginning immediately after the application and for the duration of the initial waiting period of preferably about 3 minutes before separating the layers. The initial waiting period may be about or greater than about 3 minutes or any time sufficient to allow filtration of the entire fluid sample.

One advantage of the inventive multilayer device is the absence of the use of a centrifuge to separate the different components of a fluid sample such as whole blood. Centrifuging a whole blood fluid sample allows for the separation of, for example, red blood cells from plasma. However, this is a cumbersome step, moreover a much larger fluid sample volume is needed. The multilayer device described here allows for a simple method of quickly obtaining plasma without the use of centrifugation or an excessively large fluid sample volume. Accordingly, this simple application, in one embodiment, allows for in and out of competition tests in anti-doping. Another embodiment for this application is in the use of drug discovery and development in, for example, the pharmaceutical technology.

An obstacle in available methods in the art is that a sample volume must be consistent and within a limited volume range. If too little or too much fluid volume is applied for testing, the analysis may not be accurate or may have null results. However, one of the advantages of the inventive multilayer device is its capacity for accurately and quantitatively processing a wide and flexible application volume, where the need to ensure accurate volumes sampled during sample collection is eliminated. The robustness of the multilayer device is greatly improved over current methods in the art. For example, the flexible sample application volume useful for the subject multilayer device may be, but not limited to, about 10 microliters to about 50 microliters of whole blood, where each cutout area of a multilayer device may receive varying volumes and still result in an accurate analysis.

An unfortunately low volume of a collected sample for subsequent analyses has been another hindrance in the art. However, in an advantageous embodiment, the subject multilayer device described here was found capable of not only processing a large and flexible sample volume, but also collecting a large volume of, for example, plasma from the collection material. For example, the collected volume may be, but not limited to, about or greater than about 4 microliters to about 15 microliters, for example, about 4.6 microliters to about 14.7 microliters. Table 3 demonstrates the initial whole blood volume and resulting collected plasma using a multilayer device comprising two filtration membranes, where 0.3 microliters plasma to microliters blood is about 3-fold greater than the prior art. The quantity of red blood cells (RBC) collected is a direct function of the volume of whole blood applied to a multilayer device described here, such as from a finger prick which could contain a whole blood sample volume ranging from about 5 µl to about 100 µl, more generally about 10 µl to about 50 µl, and the hematocrit of the collected whole blood sample. Hematocrit is the percent of RBC in the blood, with the balance being plasma. Hematocrit can range from about 30% to about 80% in a whole blood sample, more generally about 30% to about 60%.

The multilayer device described here overcomes the issues related to sample collection. Since only a small fluid sample volume is necessary for testing, a phlebotomist is not required. A sample, for example, of whole blood, may be obtained by first sterilizing the area to be pierced with an alcohol wipe and piercing the area of a finger or a heel with a sterile, disposable lancet, otherwise known as whole blood microsampling. Microsampling is a technique primarily used in mammals, such as for example, rodents, dogs, horses, and humans, that reduces the routine blood volume collected without any measurable effects to the subject regardless of the subject's size. These benefits of micro sampling are especially relevant and important for extremely ill human, neonatal and preemie infants, where regular collection of blood samples can be deleterious to the well-being of the infant. The collection of multiple samples of microliter volumes for diagnostic tests from such ill infants is much less demanding and deleterious upon their bodies than taking samples of milliliter volumes as has been the custom to date. Small liquid samples may be collected by this technique, including but not limited to, capillary microsampling, lab-on-a-chip devices, and other small volume devices. Dried matrix spots may also be collected for blood (dried blood spots—DBS), plasma (dried plasma spots—DPS), or for sweat, urine, semen, amniotic fluid, tears, etc. depicted by "X" (dried X spots—DXS).

Liquid plasma microsampling is a technique involving the collection of whole blood using for example a MYLAR® coated capillary tube, preferably containing a polymer plug, and centrifuging the tube to obtain the separation of plasma from red blood cells (depending on sample size, the red blood cells may amount to about 70 microliters) (Bowen, C. L., et al. (2012) *Proc. Of the 60th ASMS Conference on Mass Spectrometry*. Vancouver, BC. WP 493). Although the capillary collection of whole blood may be useful in the described invention, the complete technique which requires centrifugation, is not a preferred method since it does not provide a time or cost efficient means for separation and requires the added step of centrifugation. Also, liquid plasma microsampling does not provide any savings in shipping and storage costs as compared to the inventive means for collecting and separating a whole blood cell sample.

Another issue problematic in the art that the inventive multilayer device overcomes is the filtration of whole blood having a large and wide hematocrit range. In one embodiment, the invention advantageously filters whole blood having a wide and high hematocrit level of about 30% to about 60% hematocrit levels through the novel multilayer device without causing any hemolysis. A wider hematocrit range may also be filtered without having any adverse results. The unique filtration membrane unit composition allows for the processing of such a wide hematocrit range.

One of skill in the art understands the obstacles of using a DBS. However, since there are some advantages to the application and in view of a preference by pharmaceutical companies to test plasma, a novel multilayer device as described here has all of the benefits of a DBS card without any of its disadvantages. For example, hematocrit bias is hypothetically non-existent and pharmacokinetics (PK) in plasma rather than blood are advantages of the inventive multilayer device.

Analysis Applications

The multilayer device described here may be used in a variety of fields; however, the common thread is that the product may be used for a robust, efficient, and reliable bioanalysis method coupled with chromatography and spectroscopy techniques. The useful applications may include, but are not limited to, drug testing, drug discovery and development, genetic testing, forensics analysis, and the like. After microsampling, filtrating or separating, and collecting the desired components of a fluid sample, extraction of analytes were accomplished by direct elution followed by solid phase extraction (SPE) and, in some embodiments, automated analysis methods for detecting the presence of analytes of interest obtained from the filtration membrane and/or collection material layers in a fluid sample including but not limited to liquid chromatography (LC), mass spectrometry (MS), LC/MS, LC/MS/MS, and the like are applied. For example, the collection material layer containing the cellular components may also be eluted and the cellular components digested by techniques commonly known and used in the art, followed by various analyses of cell-associated proteins, peptides, DNA, RNA, etc. The multilayer device is amenable for fully automated quantitative analysis, and in one embodiment, on-line solid phase extraction coupled either directly with mass spectrometry or via SPE LC/MS/MS where a subsequent chromatographic separation of the SPE eluate occurs prior to MS or MS/MS.

The example embodiments may be implemented on computers and servers such as, for example, general purpose computers that may have, among other elements, a microprocessor (such as from the Intel Corporation, AMD or Motorola); volatile and non-volatile memory; one or more mass storage devices (i.e., a hard drive); various user input devices, such as a mouse, a keyboard, or a microphone: and a video display system. The computers and servers may be running on any one of many operating systems including, but not limited to WINDOWS, UNIX. LINUX, MAC OS, or Windows (XP, VISTA, etc.). It is contemplated, however, that any suitable operating system may be used for the present invention. In almost all cases the commercial on-line robotic systems coupled with LC/MS/MS are completely controlled by the system software. A Laboratory Information Management System (LIMS) such as, for example, THERMO SCIENTIFIC™ Watson LIMS™ is an example of an information management system for handling a large volume of data that can be acquired from the described embodiments. The computers and servers may be a cluster of web servers, which may each be LINUX based and supported by a load balancer that decides which of the cluster of web servers should process a request based upon the current request-load of the available server(s).

The computers and servers may be connected via networks, including the Internet, WAN, LAN, Wi-Fi, other computer networks (now known or invented in the future), and/or any combination of the foregoing. It should be understood by those of ordinary skill in the art having the present specification, drawings, and claims before them that networks may connect the various components over any combination of wired and wireless conduits, including copper, fiber optic, microwaves, and other forms of radio frequency, electrical and/or optical communication techniques. It should also be understood that any network may be connected to any other network in a different manner. The interconnections between computers and servers in system 100 are examples. Any device may communicate with any other device via one or more networks.

The example embodiments may include additional devices and networks beyond those disclosed. Further, the functionality described as being performed by one device may be distributed and performed by two or more devices. Multiple devices may also be combined into a single device, which may perform the functionality of the combined devices.

The various participants and elements described herein may operate one or more computer apparatuses to facilitate the functions described herein. Any of the elements in the above-described Figures, including any servers, user terminals, or databases, may use any suitable number of subsystems to facilitate the functions described herein.

Any of the software components or functions described in this application, may be implemented as software code or computer readable instructions that may be executed by at least one processor using any suitable computer language such as, for example, Java, C++, or Perl using, for example, conventional or object-oriented techniques.

The software code may be stored as a series of instructions or commands on a non-transitory computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus and may be present on or within different computational apparatuses within a system or network.

It may be understood that the present invention as described above can be implemented in the form of control logic using computer software in a modular or integrated manner. Based on the disclosure and teachings provided herein, a person of ordinary skill in the art may know and appreciate other ways and/or methods to implement the present invention using hardware, software, or a combination of hardware and software.

EXAMPLES

Example 1

Construction of Book-Type Multilayer Device

To prepare the filtration membrane unit, for example, RBC filter disks, a iPOC$^{DX}$™ membrane filter sheet was punched using HARRIS Uni-Core™ punch of 5 mm diameter (Amazon, USA). A bottom support layer comprising cutout disks of 5 mm diameter, which used the card stock material similar to the top cover or top support layer, were prepared using an OSBORNE arch punch (Amazon, USA). As shown in FIG. 1, after preparing each layer of the materials, the card was assembled by first placing a polyester hydrophobic membrane layer (4) on the inner side of the underside of a top cover card stock (2) followed by punching equally spaced four holes through the upper card stock or top cover and through the polyester hydrophobic membrane layer (4). The bottom elevated or raised supports (6) were made of two round disks of the cover support card stock material affixed on the inner surface of the bottom cover card stock (7) using an adhesive, such as for example, adhesive tape. A cellulose-based paper substrate or collection material (5) was then placed directly on top of the elevated or raised bottom supports or contact support layer, where the collection material with outlined sample placement circles were aligned with the cutout holes of the top cover and hydrophobic membrane (4). This book-type multi-layered card utilized two slightly different RBC filter membrane disks: one larger comprising a diameter of about 7 mm to about 11 mm (3) and one smaller comprising a diameter of about 4 mm to about 6 mm (1) and the final step was to place these two disks layered on the card or multilayer device. The larger disks (3) were inserted in between the inner side of the upper card stock and the polyester hydrophobic membrane layer while maintaining alignment with the opening holes. The book-type card was then held closed such that all of the layers were in contact. A multilayer device may utilize temporary binders such as for example, four paper clips, to achieve full and complete closure. Finally, the smaller filtration membrane disks were placed on the outer side of the upper card stock or top cover where the opening holes are located. A fluid biological sample could then be placed within the holes of the top cover and on the filtration membranes.

The multilayer device card consisted of a folded card stock (0.350 mm thickness×76.2 mm W×50.8 mm L) which has a function to support layers of different materials. For the purpose of illustration, the upper and lower support layers or support covers of the folded card stock are shown in detached form in FIG. 2. Viewed from the upper surface, the filtration membrane unit comprising two filtration membranes or iPOC$^{DX}$™ filter disks (layers 1 and 3) featured asymmetric pore dimensions. The upper disk or first filtration membrane (layer 1) was the thinner iPOC$^{DX}$™ X membrane (35 μm top, 5 μm bottom) and positioned in close contact directly above the lower disk or second filtration membrane (layer 3) which was iPOC$^{DX}$™ S/G membrane disk, 35 μm top, 2.5 μm bottom. When combined to form a filtration membrane unit, the two disks can sequentially and effectively filter out the RBC from whole blood with Hct up to 60% without showing any evidence of hemolysis. The different sizes of the two disks (upper—4 to 5 mm diameter and bottom—7 to 11 mm diameter) were selected to accommodate variable sampling volumes and provide the flexible sampling volume feature for the card.

Should a non-uniform filtration rate be problematic at different Hct levels, the filtration membranes may be modified to circumvent this issue. For example, a pinhole was punctured through the upper iPOC$^{DX}$™ X membrane to create a small through-hole to provide a more uniform flow across various whole blood Hct values. The upper card stock or top cover or support layer (layer 2) was punched to create card-stock openings which match the diameter of the filtration membrane or iPOC$^{DX}$™ X membrane. The function of these openings was to securely position the first filtration membrane, iPOC$^{DX}$™ X membrane, centered above the second filtration membrane, iPOC$^{DX}$™ S/G membrane. An AHLSTROM™ 3256 (layer 4) polyester hydrophobic membrane layer (0.058 mm thickness×76.2 mm W×25.4 mm L) was punched to create open holes of 5 mm diameter and held in place by an AVERY™ 5667 easy-peel adhesive tape. This polyester hydrophobic membrane layer was used for 1) holding the second filtration membrane, iPOC$^{DX}$™ S/G membrane filter, in place and 2) attaining round, homogenous plasma or sample spots on the collection material. When a drop of blood was applied to the filtration membrane unit or filter disks, visual inspection showed rapid diffusion and absorption of blood through the first filtration membrane disk in less than 30 seconds. It was also noted that plasma diffused more rapidly than RBC at the horizontal plane resulting in plasma overflow through the edge of the second filtration membrane, iPOCD$^{DX}$™ S/G membrane disk and onto the collection material paper substrate. Without the hydrophobic membrane polyester layer, this flow pattern caused the initiation of plasma absorption and spreading starting from the edge of the filtration membrane unit disk onto the collection material paper substrate and thus resulted in an inhomogeneous plasma spot shape, for example, a semi-full circle or horseshoe-shaped spots. To avoid this, the hydrophobic membrane polyester layer was placed in between the second filtration membrane, iPOC$^{DX}$™ S/G disk, and collection material paper substrate. With the 5-mm opening holes on the hydrophobic membrane polyester and 7 mm second filtration membrane, iPOC$^{DX}$™ S/G disks, there was close contact between the second filtration membrane, iPOC$^{DX}$™ S/G disk, and collection material cellulose paper substrate, yet a 2 mm offset from the 7 mm second filtration membrane, iPOC$^{DX}$™ S/G disk, prevented direct contact between the edge of the second filtration membrane, iPOC$^{DX}$™ S/G disk, and the collection material paper substrate. In this way, round, homogenous plasma spots were produced without any evidence of hemolysis. The thinness of the polyester hydrophobic membrane played an important role as well by maximizing the close contact between the collection material paper substrate and the second filtration membrane, iPOCD$^{DX}$™ S/G membrane. The cellulose-based paper substrate collection material (layer 5) was an AHLSTROM™ grade 601 paper (0.190 mm thickness×76.2 mm W×25.4 mm L) made from cotton linter pulp. The contact support layer containing raised supports (layer 6) positioned intimately underneath the collection material paper substrate was made of a stack of two round disks obtained from card stock (11 mm diameter bottom disk and 5 mm diameter top disk) held in place and in alignment with the filtration membrane unit, iPOC$^{DX}$™ membrane filter disks, by an AVERY™ 8665 adhesive tape (76.2 mm W×25.4 mm L), but may be adhered by any means as long as the adhesive does not interfere with filtration, spotting, or analyses. The function of the bottom contact support is to ensure a close physical contact between the collection material paper substrate and the filtration membrane unit, more specifically the second filtration membrane, iPOC$^{DX}$™ S/G membrane. This book-type multilayer device has the capacity to produce up to 4 plasma spots and/or controls per card as shown in FIG. 1 or FIG. 2. The multilayer device card was constructed to produce 3 plasma spots because the employed 4 mm clamp size has the clamp-head washing positions configured at spot position 4.

Example 2

Automated Flow-Through Elution Coupled with on-Line SPE-LC-MS/MS Bioanalysis of Opioids and Stimulants in Blood In order to design, develop, and validate a hematocrit-capable multilayer device that can produce plasma without the need for centrifugation that is suitable for automated on-line liquid chromatography with tandem mass spectrometry detection (LC/MS/MS) analysis, a multilayer device was developed to prepare dried plasma spot samples from whole blood microsampling. Extraction of the resulting dried plasma spot was accomplished by direct elution followed by an on-line solid phase extraction (SPE) and LC/MS/MS determination of analytes of interest, in this case, opioids and stimulants. Four opioids and five stimulants having varying physiochemical properties were selected to test in this analysis.

A series of standard working solutions were prepared by dilution of primary stock solutions with 3:7 methanol/water (v/v). Calibration standards were also prepared at 5 ng/mL, 10 ng/mL, 25 ng/mL, 50 ng/mL, 100 ng/mL, 250 ng/mL, 500 ng/mL, and 1,000 ng/mL. Quality control (QC) samples were prepared at 5 ng/mL, 15 ng/mL, 300 ng/mL, and 900 ng/mL.

Sample preparation for 30%, 45%, and 60% hematocrit (Hct) blood occurred by measuring the initial hematocrit (Hct) level on a hematocrit measuring device—the StatSpin™ CritSpin™ (Thermo Fisher Scientific; Waltham, MA, USA). The Hct level of whole blood samples were measured. Whole blood was placed into capillary tubes and spun in the device at 13,700×g for 2 min. After centrifugation, the Hct level was measured using the device. To prepare blood with 30%, 45%, and 60% Hct, 1 mL of blood was placed into a 2 mL LoBind EPPENDORF™ tube and spun at 3000×g-5000×g for 3 min to fractionate RBC from plasma. With the measured level of the initial Hct, calculation was carried out to determine how much plasma was to be added to or removed from the 1 mL centrifuged blood in order to achieve the desired Hct levels. After adjusting the plasma volume, different Hct level sample tubes were then gently mixed on a vortex mixer and 500 µL were transferred to 1.5 LoBind EPPENDORF™ for standards fortification according to the sample preparation method described above. Evaluation of Hct effect was performed at LLOQ QC and HQC. The calibration curves were prepared using blood with 42% Hct.

All samples were prepared by fortifying 500 µL of blood containing Na$_2$EDTA with 10 µL of a working solution in 1.5 mL LoBind Eppendorf tubes. Fortified samples were subsequently incubated at 37° C. with 200 rpm agitation for 30 min. Eight-point calibrators were 5 ng/mL, 10 ng/mL, 25 ng/mL, 50 ng/mL, 100 ng/mL, 250 ng/mL, 500 ng/mL, and 1000 ng/mL while the QC samples were 5 ng/mL at LLOQ QC, 15 ng/mL at Low QC (LQC), 300 ng/mL at Medium QC (MQC), and 900 ng/mL at High QC (HQC). After incubation, samples were set aside at room temperature for 30 min prior to DPS preparation using the book-type DXS cards or multilayer device as shown in FIG. 1.

Briefly, with the multilayer device in a closed position, an aliquot of blood (about 10 µL to about 50 µL) was applied to the upper filtration membrane disk within the cutout holes of the top cover, and the multilayer device remained in the closed position for 3 min to complete the filtration process. Next, the collection material or cellulose paper substrate containing filtered plasma was retrieved. In this example, the collection material was affixed to an appropriate paper card stock, which was a Perkin Elmer 226 card with the sampling window removed or online-amenable window support layer. Alternatively, the collection material is pre-affixed to the online-amenable window support layer. Any card stock that meets the DBSA's automated configuration criteria can be used.

In a 1.5 mL EPPENDORF™ tube, 10 microliters (µl) of the working solution was added to 500 µl of whole blood fortified with anti-coagulant. Samples were then incubated at 37° C. for 30 minutes at 200 rpm agitation speed. Samples were equilibrated at room temperature for at least 30 minutes prior to dried plasma spot preparation.

Dried plasma spots were prepared by applying an aliquot (about 15 µl to about 50 µl) of whole blood sample to a closed multilayer device within each of the cutout circles for collecting fluid samples, i.e., on a filtration membrane unit. After 3 minutes, the multilayer device was opened. The plasma had been absorbed onto the collection material forming a dried plasma spot. The collection material containing the dried plasma spot was removed and allowed to dry further at room temperature for 30 minutes prior to automated on-line analyte analysis. It was noted that the 60% hematocrit level sample did not have hemolysis.

Analytes of interest (and internal standard) included morphine (and morphine-d$_3$), codeine (and codeine-d$_3$), oxycodone (and oxycodone-de), hydrocodone (and hydrocodone-d3), amphetamine (and amphetamine-d$_5$), methamphetamine (and methamphetamine-d$_5$), 3,4-methylenedioxymethamphetamine (MDMA) (and MDMA-d$_5$), phentermine (and phentermine-d$_5$), and mephedrone (and mephedrone-d$_3$).

The feature of flexible sampling volume. As described above, the construction of the book-type multilayer device card utilized two RBC filtration membrane disks (iPOC$^{DX}$™ X and S/G membrane filters) to sequentially and efficiently filter out RBC for samples having up to a 60% Hct level and obtain plasma. The size of the disks can be determined depending on the application volume. The critical point is to avoid over fill or under fill of the disk with blood. Over fill will cause over saturation of filtration capacity resulting in whole blood overflows through the edge of the disk. If under filled, a fraction of plasma will be retained in the disk resulting in less available collected plasma and may result in an incomplete saturation of the plasma collection material substrate. Incomplete saturation will then result in analytical imprecision. Thus, test whether or not the multilayer device's capacity for a flexible sample application volume range (low, medium, and high), samples for four different combinatory sizes of the 2 filters were evaluated. The combinations of 4 mm and 6 mm, 5 mm and 7 mm, 5 mm and 9 mm, and 5 mm and 11 mm were evaluated for 10 µL, 12.5 µL, and 15 µL: 15 µL, 17.5 µL, and 20 µL; 20 µL, 27.5 µL, and 35 µL: and 35 µL, 42.5 µL, and 50 µL blood, respectively. Three replicates (three dried plasma spots) per applied volume were prepared using volunteers' blood with 45% Hct fortified at the HQC level. Calibration curves (n=2) were prepared using the 5 mm and 7 mm combination for 20 µL applied volume. The ability to adjust the sizes of the two filter disks provides the feature of flexible sampling volume in the multilayer device.

Plasma volume yield. To measure how much plasma was produced from a sample of whole blood using the multilayer device card, plasma spots (n=2) were prepared by spotting plasma obtained from centrifuged whole blood (3 µL, 5 µL, 10 µL, 15 µL, 20 µL, and 30 µL) directly onto a small piece of collection material or paper substrate. The piece of paper substrate was weighed prior to and immediately after spotting. These data were used to plot a calibration curve of plasma volume versus weight. For the multilayer device or card samples, plasma spots (n=2) generated from the book-type multilayer device or cards using 15 µL, 20 µL, 30 µL, and 50 µL blood were weighed before and immediately after application. The measured weights were used to calculate the plasma volume yields. The multilayer device generated about 4 µL to about 15 µL of plasma volume depending on the initial whole blood volume and an average plasma volume to blood volume ratio of about 0.3, i.e., about three times that of the NOVIPLEX™ DPS card. Exemplary plasma volume yields are shown in Table 3. To evaluate if analyte concentration is affected by the elution position, center and peripheral elution positions in a spot were compared.

Center and peripheral sampling positions were calculated for morphine, codeine, oxycodone, hydrocodone. AH 7921, and fentanyl in whole blood. All calculated values as exemplified in FIG. 3 passed the acceptable criteria for % RE and % CV except for morphine which had a % RE of −17%. The fortified level was 150 ng/mL for all opioids except for fentanyl which had a fortified level of 15 ng/mL. The concentration distribution within a spot was found to have significantly less variation in comparison to DBS where the difference between center and peripheral positions can be up to 50%.

Method Validation. Adopting the U.S. FDA guidelines (FDA. *Guidance for Industry—Bioanalytical Method Validation: UCM368107* 2013, 1-34), linearity, precision, accuracy, carry-over, selectivity, recovery, and stability were investigated to validate the functionality of the developed DPS card for a fully automated on-line analysis. Regulatory guidelines define the acceptance criteria as within ±15.0% relative error (RE) for accuracy and ≤15% coefficient of variation (CV) for precision for all QC levels except the LLOQ QC which has ±20.0% RE and ≤20% CV (Id.). Relative error percentages (% RE) were calculated by (measured mean/nominal value)−1×100) and coefficient of variation percentages (% CV) were calculated by (standard deviation/mean)×100.

Short term on-card stability. A short-term stability study was conducted to evaluate the on-card stability of the studied opioids and stimulants. The evaluation was carried at 0, 3, 9, 14, and 28 days at the LLOQ and HQC QC levels (n=3) at three different storage conditions: at room temperature (RT) kept in a box filled with continuous flow of nitrogen (RT+Nitrogen); at RT kept in a glassine envelope with desiccant which was then sealed in a Ziploc® bag (RT+Air); and at −20° C. kept in a glassine envelope with desiccant sealed in a Ziploc® bag (−20° C.+Air). Samples were evaluated at 0 days, 3 days, 9 days, 14 days, and 28 days. At each time point, a fresh calibration curve was prepared. A minor decrease was noted for the same analytes when stored at −20° C.+air. This suggested that the analyte on-card instability or decomposition is due to oxidation. A solution for avoiding instability or decomposition of the analytes in a sample, long term storage of the multilayer device may be in a nitrogen filled container. Removing oxygen will then prevent the detriments of oxidation. Results indicated that multilayer device on-card stability is analyte-dependent and storage-dependent as shown in FIG. 4 and FIG. 5. FIG. 4 showed on day 28 significant decomposition (analysis of variance, ANOVA) for oxycodone (p=0.001), hydrocodone (p=0.004), and mephedrone (p<0.0001) when stored in the presence of air (RT+Air and −20° C.+Air). When stored at RT+$N_2$, on-card stability can be attained for all nine analytes for 28 days. FIG. 5 showed on day 28, significant decompositions (ANOVA, p<0.0001) for oxycodone, hydrocodone, and mephedrone when stored in the presence of air (RT+Air and −20° C.+Air). When stored at RT+air, decompositions (>50%) were noted for oxycodone, hydrocodone, and mephedrone by day 3. may be due to oxidation and that sub-zero ° C. may slow the decomposition rate. Recently, similar on-card decomposition pattern for mephedrone in relation to the effects of storage conditions in the presence of air versus $N_2$ has been reported (Verplaetse, R.: Henion, J. *Analytical Chemistry*, 2016, 88, 6789-6796.

Hematocrit effects. One of the major concerns reported for DBS applications is the Hct issues for which a number of possible solutions have been proposed (De Kesel, P. M., et al. *Bioanalysis* 2013, 5, 2023-2041; "De Kesel"). Of the proposed solutions, DPS was one of the promising alternatives (Déglon. J., et al. *Bioanalysis* 2015, 7, 2375-2385). To evaluate if the book-type multilayer device card of the invention was Hct compatible, blood samples with 30%, 45%, and 60% Hct were prepared and fortified at LLOQ QC and HQC levels. Results showed no Hct bias at both QC levels for all analytes as shown in FIG. 6. The red line of FIG. 6 indicates the maximum acceptable criteria of ≤20.0% RE and CV at the LLOQ and ≤±15.0% RE and CV at high QC. No hematocrit bias was observed at the Hct range of 30 to 60%. Compared to a previously developed card (Sturm, R., et al. *Bioanalysis* 2015, 7, 1987-2002), this book-type DPS card appears to provide a wider range of Hct applicability which is accomplished through a preferred design incorporating two filtration membranes or RBC filter disks, which can filter and capture RBCs.

Flexible sampling volume feature. A 4-mm partial spot analysis was employed. With a partial spot analysis, a 4-mm spot area is sampled within a dried plasma spot. So, if a plasma spot is homogenous, accuracy of the results should not be affected by whether the 4-mm sampling area was taken partially from an 8 mm or a 14 mm plasma spot and whether the 4-mm sampling area was acquired from the center or the peripheral region within a dried plasma spot. To support this postulate, blood volumes ranging from 10 to 50 µL which produced plasma spot sizes of ca. 8 to 14 mm were evaluated using the book-type multilayer device. The book-type multilayer device were customized to have different filtration membrane sizes of a first filtration membrane, X. and a second filtration membrane, S/G, disks in order to accommodate different blood volume. Quantitation was performed with a calibration curve constructed from 20 µL of blood using multilayer device cards with 5 mm and 7 mm filtration membranes. X and S/G disks, respectively. Comparable accuracy at HQC was observed among different applied whole blood volumes. Although a majority of % RE were within the acceptance limit (≤±15%), trends of negative biases were observed from spots produced with <20 µL blood while positive biases at spots produced from >20 µL blood. These biases can be corrected by preparing a calibration curve using a volume that is comparable to the sample applied volume. Center versus peripheral spot positions were also evaluated at 4 different application volume (15 µL, 20 µL, 35 µL, and 50 µL) producing different plasma sizes.

Results in TABLE 2 showed no differences in the measured levels for all analytes between the center and peripheral positions at 4 different applied blood volume or various plasma spot sizes. Previous studies have reported similar results where comparable data were obtained from spots prepared from spotting 20 µL, 25 µL, and 30 µL centrifuged plasma using the SAFECAP® capillary tube (Li, W., et al. *Journal of Chromatography B—Analytical Technologies in the Biomedical and Life Sciences* 2015, 991, 46-52, "Li et al., 2015"). Although comparable results were observed for 20 µL, 25 µL, and 30 µL plasma, a negative bias was observed at 10 µL plasma (Li et al., 2015). The type of cellulose paper substrate used in that study was the DMPK C card which is nearly 2.5 times thicker than the collection material or paper substrate (AHLSTROM™ Grade 601) used in the book-type multilayer device card. When a thicker paper substrate is employed, the spreading and penetration of the plasma throughout the paper may undergo incomplete penetration described by Henion et al. (Henion, J., et al. *Bioanalysis* 2013, 5, 2547-2565). If so, inaccuracy would be more of an issue at a smaller volume than a larger volume. Noticeably, results reported in Table 1 and Table 2 support the rationale that plasma consistency is independent of both the Hct level in blood and the applied blood volume and show the functional feature of flexible sampling feature in the application of the book-type multilayer device card.

TABLE 1

Flexible Sampling Volume: Different Ranges of Blood Application Volume Using Different Sizes of Filtration Membranes

| Applied Blood Volume | Morphine ng/mL | RE | Codeine ng/mL | RE | Oxycodone ng/mL | RE | Hydrocodone ng/mL | RE | Amphetamine ng/mL |
|---|---|---|---|---|---|---|---|---|---|
| Membrane sizes: 4 and 6 mm | | | | | | | | | |
| 10.0 µL | 806.1 | −10.4% | 790.7 | −12.1% | 849.3 | −5.6% | 887.3 | −1.4% | 843.4 |
| 12.5 µL | 782.0 | −13.1% | 769.1 | −14.5% | 799.1 | −11.2% | 867.1 | −3.7% | 788.6 |
| 15.0 µL | 883.4 | −1.8% | 838.9 | −6.8% | 880.5 | −2.2% | 955.4 | 6.2% | 878.5 |
| Membrane sizes: 5 and 7 mm | | | | | | | | | |
| 15.0 µL | 759.4 | −15.6% | 759.7 | −15.6% | 796.5 | −11.5% | 846.1 | −6.0% | 790.3 |
| 17.5 µL | 770.2 | −14.4% | 764.4 | −15.1% | 775.4 | −13.8% | 861.9 | −4.2% | 773.1 |
| 20.0 µL | 800.3 | −11.1% | 773.3 | −14.1% | 854.7 | −5.0% | 900.1 | 0.0% | 846.8 |
| Membrane sizes: 5 and 9 mm | | | | | | | | | |
| 20.0 µL | 824.8 | −8.4% | 756.6 | −15.9% | 803.6 | −10.7% | 863.8 | −4.0% | 818.5 |
| 27.5 µL | 913.2 | 1.5% | 895.7 | −0.5% | 933.6 | 3.7% | 1012.4 | 12.5% | 905.6 |
| 35.0 µL | 993.7 | 10.4% | 949.7 | 5.5% | 996.2 | 10.7% | 1061.2 | 17.9% | 967.8 |
| Membrane sizes: 5 and 11 mm | | | | | | | | | |
| 35.0 µL | 876.9 | −2.6% | 810.1 | −10.0% | 839.2 | −6.8% | 886.6 | −1.5% | 898.0 |
| 42.5 µL | 1013.6 | 12.6% | 962.4 | 6.9% | 1005.5 | 11.7% | 1060.4 | 17.8% | 1040.7 |
| 50.0 µL | 1006.5 | 11.8% | 958.7 | 6.5% | 993.7 | 10.4% | 1090.5 | 21.2% | 1031.0 |

| Applied Blood Volume | Amphetamine RE | Methamphetamine ng/mL | RE | MDMA ng/mL | RE | Phentermine ng/mL | RE | Mephedrone ng/mL | RE |
|---|---|---|---|---|---|---|---|---|---|
| Membrane sizes: 4 and 6 mm | | | | | | | | | |
| 10.0 µL | −6.3% | 823.0 | −8.6% | 823.3 | −8.5% | 879.0 | −2.3% | 870.0 | −3.3% |
| 12.5 µL | −12.4% | 773.1 | −14.1% | 777.7 | −13.6% | 820.0 | −8.9% | 828.0 | −8.0% |
| 15.0 µL | −2.4% | 851.5 | −5.4% | 872.4 | −3.1% | 883.4 | −1.8% | 887.0 | −1.4% |
| Membrane sizes: 5 and 7 mm | | | | | | | | | |
| 15.0 µL | −12.2% | 778.1 | −13.5% | 798.7 | −11.3% | 770.1 | −14.4% | 822.7 | −8.6% |
| 17.5 µL | −14.1% | 767.3 | −14.7% | 794.9 | −11.7% | 811.6 | −9.8% | 820.8 | −8.8% |
| 20.0 µL | −5.9% | 816.0 | −9.3% | 812.9 | −9.7% | 852.5 | −5.3% | 881.7 | −2.0% |

TABLE 1-continued

Flexible Sampling Volume: Different Ranges of Blood Application Volume Using Different Sizes of Filtration Membranes

| Membrane sizes: 5 and 9 mm | | | | | | | | |
|---|---|---|---|---|---|---|---|---|
| 20.0 μL | −9.1% | 787.9 | −12.5% | 825.8 | −8.2% | 765.5 | −14.9% | 876.2 | −2.6% |
| 27.5 μL | 0.6% | 907.2 | 0.8% | 932.2 | 3.6% | 893.6 | −0.7% | 1001.3 | 11.3% |
| 35.0 μL | 7.5% | 958.9 | 6.5% | 985.3 | 9.5% | 961.5 | 6.8% | 1025.3 | 13.9% |
| Membrane sizes: 5 and 11 mm | | | | | | | | |
| 35.0 μL | −0.2% | 883.7 | −1.8% | 876.4 | −2.6% | 881.3 | −2.1% | 874.1 | −2.9% |
| 42.5 μL | 15.6% | 1020.9 | 13.4% | 993.9 | 10.4% | 1029.9 | 14.4% | 1023.0 | 13.7% |
| 50.0 μL | 14.6% | 995.8 | 10.6% | 982.1 | 9.1% | 997.3 | 10.8% | 1017.7 | 13.1% |

Filtration membrane sizes referred to the first filtration membrane, X, and second filtration membrane, S/G, disks in diameter. For quantitation, calibration curve was built using a book-type multilayer device card with a 5 mm and 7 mm filtration membrane combination and 20 μL whole blood.

TABLE 2

Center Versus Peripheral Spot Elution Positions for Different Sizes of Plasma Spots Generated from a Range of Whole Blood Volumes

| Blood Volume | Spot Elution Position | Normalized value | | | | | | | | |
|---|---|---|---|---|---|---|---|---|---|---|
| | | Morphine | Codeine | Oxycodone | Hydrocodone | Amphetainine | Methamphetamine | MDMA | Phentermine | Mephedrone |
| 15 μL | Center | 100% | 100% | 100% | 100% | 100% | 100% | 100% | 100% | 100% |
| 15 μL | Peripheral | 100% | 111% | 108% | 112% | 108% | 105% | 104% | 100% | 109% |
| 20 μL | Center | 100% | 100% | 100% | 100% | 100% | 100% | 100% | 100% | 100% |
| 20 μL | Peripheral | 99% | 106% | 98% | 101% | 96% | 95% | 102% | 96% | 98% |
| 35 μL | Center | 100% | 100% | 100% | 100% | 100% | 100% | 100% | 100% | 100% |
| 35 μL | Peripheral | 101% | 112% | 108% | 110% | 104% | 105% | 101% | 105% | 106% |
| 50 μL | Center | 100% | 100% | 100% | 100% | 100% | 100% | 100% | 100% | 100% |
| 50 μL | Peripheral | 98% | 107% | 104% | 104% | 98% | 97% | 100% | 96% | 99% |

Fortified level was at HQC (900 ng/mL). For quantitation, calibration curve was built using the membrane sizes of 5 and 7 mm combination with 20 μL whole blood application volume. The measured levels were normalized to the center position sample as 100%.

The book-type multilayer device versus existing DPS cards. The two closest existing DPS cards to that of the multilayer device described here are the NOVIPLEX™ card, which is commercially available from Novilytic LLC (Kim, J. H., et al. *Anal Chem* 2013, 85, 11501-11508) and the 'auto DPS card' previously reported by Sturm et al. (*Bioanalysis* 2015, 7, 1987-2002). In general, the conceptual design of these two cards and the inventive multilayer device card is similar as each of them employs an on-card membrane filtration technique to separate RBC from plasma. However, the card structures and production of plasma in each card format are different. For a successful on-card plasma spot production, the inventive book-type multilayer device card does not require any external device. Although the NOVIPLEX™ card also does not require any external device for generation of plasma spots, the sample handling process is tedious as it requires a pair of tweezers to remove the small 2-mm disk and manually transfer the disk for further sample extraction processes as the NOVIPLEX™ card is not compatible for automated analysis. While the yield of plasma volume by auto DPS was not determined, the NOVIPLEX™ card requires a minimum of 25 μL blood to produce about 2.5 μL plasma (Kim, J. H. et al. *Anal Chem* 2013, 85, 11501-11508). That is 0.100 μL plasma per p L blood. Whereas, the book-type multilayer device card of the invention produces a larger amount of plasma volume (4.6 μL to 14.7 μL depending on the initially applied blood volume and averaging about 3 fold greater plasma/blood volume ratio, i.e., 0.303±0.007 plasma per μL whole blood (TABLE 3).

TABLE 3

Determination of Plasma Volume Generated from a Multilayer Device

| iPOC$^{DX}$™ | | membranes (mm) | Whole blood volume (μL) | Plasma volume (μL) | Plasma/blood volume Ratio |
|---|---|---|---|---|---|
| X | | SG | | | |
| 4 | | 6 | 15 | 4.55 | 0.304 |
| 4 | | 6 | 15 | 4.71 | 0.314 |
| 5 | | 7 | 20 | 6.18 | 0.309 |
| 5 | | 7 | 20 | 5.95 | 0.298 |
| 5 | | 9 | 30 | 9.07 | 0.302 |
| 5 | | 9 | 30 | 9.22 | 0.307 |
| 5 | | 11 | 50 | 14.72 | 0.294 |
| 5 | | 11 | 50 | 14.68 | 0.294 |

The calibration curve was plotted for the weight of plasma spots against plasma volume ranging from 3 μL to 30 μL.
The carve showed linearity with an $R^2 = 0.9994$, slope = 0.9793 x 0.0995.

The Automated Flow-through Spot Elution and On-line SPE. The robotic system employed in this work was described previously (Verplaetse, R.; Henion, *J. Drug Testing and Analysis* 2016, 8, 30-38: Sturm, R. et al. *Bioanalysis* 2015, 7, 1987-2002; Oliveira, R V. et al. *Anal Chem* 2014, 86, 1246-1253). Briefly, it included an automated flow-through elution of dried spots on a cellulose card using the DBSA system (Spark Holland, Emmon, The Netherlands). This system picked up a collection material affixed to an online-amenable window support of a multilayer device card, located the dried spots on the card followed by spot solvent elution coupled to an in line SPE analyte trap/elution step. Spot desorption was performed by a flow through mechanism where a pair of clamps (equipped with tubing for solvent delivery) formed a clamped elution area on the collection material paper substrate. In the clamping position, the elution solvent was introduced through the collection material paper and the extract was delivered to the in-line SPE cartridge. A detailed illustration and description of the entire online system is incorporated by reference (Verplaetse, R; Henion, *J. Drug Testing and Analysis* 2016, 8, 30-38). In the current study, a partial spot analysis using 4 mm clamp size coupled to either the invisible or user-defined spot recognition modes was employed. There were four spots per collection material/online-amenable window support card featuring spots no. 1, 2, and 3 as dried plasma spots and spot no. 4 as the clamp washing positions, which were carried out between samples. The fourth spot or cutout area comprised of 3 small circles positioned in a triangle formation for clamp washing. If a 2 mm clamp size was used, washing position was at the right corner of each spot thus providing the capacity of four sample spots per card. The 4 mm clamp size was chosen for enhanced analytical sensitivity for morphine. Spot elution was performed with 2 mL of desorption solvent (0.2% $NH_4OH$+2.5% MeOH in $H_2O$) at 100° C. and at 4 mL/min. A sample loop containing 20 µL deuterated IS solution was introduced directly into the spot elution line. Subsequently, the elution solvent was loaded to a pre-conditioned (1 mL MeOH and 1 mL desorption solvent at a 4 mL/min) SPE cartridge (HySphere® C8HD, 7 µm, 2×10 mm, Spark Holland). An LC gradient was used to elute the targeted analytes from the cartridge onto the LC column for subsequent chromatographic separation. To minimize carry over, both the SPE cartridge and the DBS clamps were sequentially washed with the following 3 different solvents (2 mL desorption solvent, 4 mL $H_2O$:MeOH ACN:IPA 2:4:3:1 v/v with 0.1% FA and finally 2 mL 0.1% FA $H_2O$) at 6 mL/min in between runs.

LC-MS/MS. LC-MS/MS analysis was performed with a NEXERAX® UHPLC system coupled to an LC-MS 8050 mass spectrometer (Shimadzu. MD, USA). Data processing was performed using Shimadzu's LabSolutions software. The LC column was a KINETEX® F5 (2.6 µm, 2.1×50 mm) equipped with a guard F5 column (2.6 µm, 2.1×5 mm) from PHENOMENEX® (Torrance, CA, USA). The mobile phase consisted of (A) 5 mM ammonium formate and 0.1% FA and (B) MeOH. The LC gradient program was: 10% B at the initial condition, 10% B at 0.25 min, 40% B at 1.70 min, 100% B at 2.20 min, 100% B at 2.48 min, and recycled back to 10% B at 2.90 min. The first 0.25 min of the flow which passed through the on-line SPE cartridge was scheduled to the waste port. The flow rate was 0.4 mL/min while the HPLC column was maintained at 50° C. The mass spectrometer was operated in the positive ion electrospray ionization mode under the following instrumental conditions: interface voltage of 0.5 kV, interface temperature of 400° C., desolvation line temperature of 100° C., heat block temperature of 140° C., drying gas flow of 3 L/min $N_2$, nebulizing gas flow of 2 L/min $N_2$ and heating gas flow of 20 L/min $N_2$. For each compound, two SRM transitions were monitored as listed on TABLE 4.

TABLE 4

Structures, Physical Characteristics and Selected m/z values for the Studies Opioids and Stimulants

| Analyte | Structure | pKa | Precursor ion (mz) | SRM productions (mz) |
|---|---|---|---|---|
| Morphine (−40 CE) | 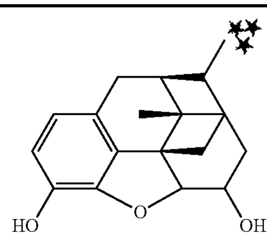 | 7.9 (base) | 286.1 | 165.1 and 201.1 |
| Morphine-d$_3$ (−40 CE) | | 9.6 (acid) | 289.1 | 165.1 and 201.1 |
| Codeine (−45 CE) | 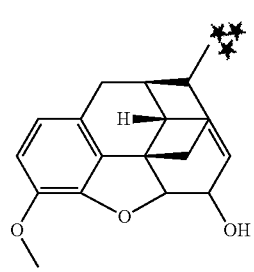 | 8.2 | 300.1 | 165.1 and 215.1 |
| Codeine-d$_3$ (−45 CE) | | | 303.1 | 165.1 and 215.1 |
| Oxycodone (−29 CE) | 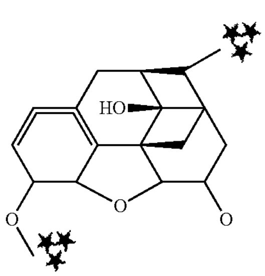 | 8.5 | 316.1 | 241.0 and 256.1 |
| Oxycodone-d$_6$ (−29 CE) | | | 322.1 | 247.1 and 262.1 |

TABLE 4-continued

Structures, Physical Characteristics and Selected m/z values for the Studies
Opioids and Stimulants

| Analyte | Structure | pKa | Precursor ion (mz) | SRM productions (mz) |
|---|---|---|---|---|
| Hydrocodone (−31 CE) | 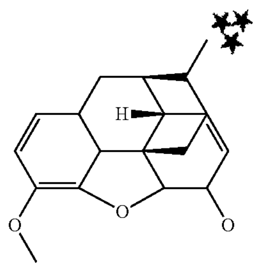 | 8.9 | 300.1 | 199.1 and 171.0 |
| Hydrocodone-d$_3$ (−31 CE) | | | 303.1 | 199.1 and 171.0 |
| Amphetamine (−35 CE) | 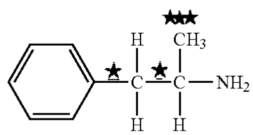 | 10.1 | 136.1 | 91.05 and 119.1 |
| Amphetamine-d$_6$ (−35 CE) | | | 141.1 | 93.1 and 124.0 |
| Methamphetamine-(−40 CE) | 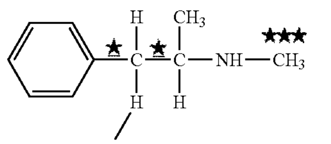 | 9.9 | 150.2 | 91.1 and 119.0 |
| Methamphetamine-d$_6$ (−40 CE) | | | 155.1 | 91.05 and 121.1 |
| MDMA-(−23 CE) | 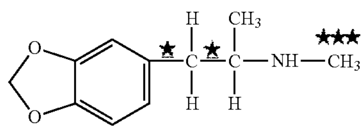 | 9.9 | 194.0 | 105.0 and 163.1 |
| MDMA-d$_6$ (−23 CE) | | | 199.1 | 107.7 and 165.0 |
| Phentermine (−40 CE) | 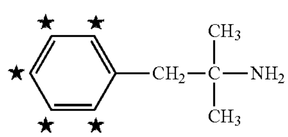 | 10.1 | 150.2 | 91.05 and 133.1 |
| Phentermine-d$_6$ (−40 CE) | | | 155.1 | 96.1 and 138.1 |
| Mephedrone-(−25 CE) | 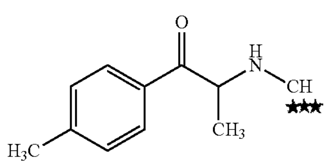 | 9.0 | 178.0 | 145.0 and 160.0 |
| Mephedrone-d$_3$ (−25 CE) | | | 181.1 | 148.5 and 163.0 |

★Indicates the position of the deuterium labels in the IS
CE = collision energy.

The instruments used for testing for the presence of analytes of interest included a dried blood spot (DBS) card autosampler (DBS. Spark Holland): high pressure dispenser pump (HPD, Spark Holland); automated SPE cartridge exchange module (ACE, Spark Holland), NEXERA® ultra-high performance liquid chromatography (UHPLC, Shimadzu); and LCMS-8050 MS (Shimadzu). Direct on-line elution of the plasma spots was conducted by clamping in the collection material containing the dried plasma spot using a clamp (4 mm), where partial spot analysis occurred at 100° C.

The Spark-Holland DBS SPE autosampler system was modified to analyze DXS samples. The system was set up in such a manner that the HPD and syringe pump were independently connected to a multi-port valve with an IS loop (20 μl of the deuterated internal standard control mixtures): another multi-port valve connected to a clamp to hold the collection material, where the clamp has a diameter of about 2 mm, which is connected to a third multi-port valve with an SPE cartridge clamp, where the third multi-port valve is also connected to an LC column, waste elimination, gradient pumps, and a computer system for online SPE-LC-HRAMS DXS extraction analyses. If an automated system is used in collaboration with the multilayer device described here, other systems besides the Spark-Holland SPE autosampler system may be used. The multilayer device may also be analyzed by using another on-line automation system, such as for example, CAMAG DBS—MS 500 (worldwideweb-.camag.com/en/dbs/dbs-ms_500.cfm)

The SPE method utilized HySphere™ C$_8$ HD, 7 μm, 2×10 mm cartridge (Spark Holland), under conditions (at 6 mL/min) of 1 milliliter methanol, 1 mL 0.2% Ammonium hydroxide and 2.5% methanol in water; elution (at 3 mL/min) of 1 mL 0.2% Ammonium hydroxide and 2.5% methanol in water; and wash (at 6 mL/min) of 2 mL 0.25 Ammonium hydroxide and 2.5% methanol in water, 4 mL 2:4:3:1 (v/v) water/methanol/acetonitrile/isopropanol. The LC program conditions (LC-MS/MS Shimadzu 8050) were as indicated in TABLE 5 below, where Pump A: 0.1% formic acid/water and Pump B: 100% methanol, where the first 0.25 minutes* of the LC gradient after passing through the SPE cartridge was directed to waste.

TABLE 5

| TIME (min) | PUMP B Concentration |
|---|---|
| Initial | 10% |
| 0.25* | 10% |
| 1.70 | 40% |
| 2.20 | 100% |
| 2.48 | 100% |
| 2.90 | 10% |

The multilayer device utilized was composed of multiple layers. The whole blood sample was applied to a first layer of a filtration membrane unit comprising a filtration membrane of an asymmetrical iPOC$^{DX}$™ X membrane (5 mm diameter of the filtration membrane disk); asymmetrical (35 µm top pore size; 5 µm bottom pore size) having a thickness of about 0.160 mm to about 0.200 mm cutout (5 mm diameter) of a top cover composed of a card stock having a thickness of 0.350 mm. The multilayer device may have 4 cutouts. The filtration membrane unit layers are confined (i.e., not flexible) cutout layers, which have the same dimensions as the top cover cutouts. Underneath the first layer of a filtration membrane unit is a second layer of a filtration membrane unit comprising a filtration membrane of an asymmetrical iPOC$^{DX}$™ S/G membrane (7 mm); asymmetrical 35 µm top pore size; 2.5 µm bottom pore size) having a thickness of about 0.260 mm to about 0.300 mm. Underneath the filtration membrane unit is a hydrophobic membrane composed of an AHLSTROM® HOLLYTEX® 3256 polyester membrane with 4 cutouts (e.g., 5 mm diameter) having the same dimensions as the circular cutouts of the top cover. This hydrophobic membrane is about 0.0584 millimeter in thickness. Underneath the hydrophobic membrane is a collection material with outlines of the cutouts but no actual confined cutouts (i.e., flexible) allowing for a flexible collection material. The collection material may be composed of AHLSTROM® 601 cellulose paper having a thickness of 0.190 mm absorbed plasma from the whole blood fluid sample. Underneath the collection material is a raised support layer which ensured a close physical contact between the filtration membrane unit, hydrophobic membrane, and collection material. The raised support layer was the cutout disks obtained from card stock with a 0.7 mm thickness being held in place using an AVERY 8665@ adhesive tape. Underneath the raised support layer was a bottom cover, which supported all of the preceding layers. The bottom layer was composed of a card stock of about 0.350 mm.

The functional application of the developed multilayer device was validated and the results demonstrated good selectivity and acceptable limits of inter-day precision and and the results demonstrated good selectivity and acceptable limits of inter-day precision and accuracy at four quality control (QC) levels. The lowest limit of detection (LLOQ) was achieved at 5 ng/mL and linearity was observed at $R^2 > 0.9964$ from 5 ng/mL to 1,000 ng/mL. The average recovery was greater than (>) 87.9%. The tested multilayer device also showed hematocrit-compatibility from 30% to 60% for the tested opioids and stimulants. A short-term stability study suggested that the multilayer device stability limited and compound-dependent when stored at room temperature in air or atmosphere.

The chromatograms of the tested four opioids and five stimulants of FIG. 7 showed internal standards having retention times (min) as shown in TABLE 6 below. FIG. 7(A) was the double blank sample, (B) was the blank sample, (C) was the LLOQ Sample (5 ng/mL), and (D) was the deuterated internal standard.

TABLE 6

| Number | Internal Standard | Retention Time (min) |
|---|---|---|
| 1 | Morphine-$d_3$ | 1.305 |
| 2 | Codeine-$d_3$ | 1.520 |
| 3 | Oxycodone-$d_6$ | 1.669 |
| 4 | Hydrocodone-$d_3$ | 1.770 |
| 5 | Amphetamine-$d_5$ | 1.731 |
| 6 | Methamphetamine-$d_5$ | 1.841 |
| 7 | MDMA-$d_5$ | 1.951 |
| 8 | Phentermine-$d_5$ | 2.037 |
| 9 | Mephedrone-$d_3$ | 2.076 |

The precision and accuracy results for the dried plasma spot analysis using blood having a hematocrit level of 30%, 45%, and 60% are presented in FIG. 6. Each of the analytes of interest for each of the different hematocrit levels was tested. Precision was evaluated by the coefficient of variation (CV) which equals the (standard deviation (SD)/mean)× 100, while accuracy was evaluated by relative error (RE) which equals the [(mean-nominal)/nominal]×100. FIG. 7 (A) shows the LLOQ QC coefficient of variation of each hematocrit level and each analyte tested and (B) shows the relative error. FIG. 7 (C) shows the High QC coefficient of variation of each hematocrit level and each analyte tested and (D) shows the relative error. A wider range of hematocrit levels was also tested. FIG. 8 and TABLE 7 below show the results of hematocrit levels from 25% to 65% as tested for morphine, codeine, oxycodone, hydrocodone, AH 7921, and fentanyl. For AH 7921 and fentanyl, recovery was found to be inversely correlated to the level of hematocrit in whole blood. While morphine, codeine, oxycodone, and hydrocodone were shown to be hematocrit compatible, AH 7921 and fentanyl were not. The same trend was observed at LQC, MQC, and HQC.

TABLE 7

| | Morphine | Codeine | Oxycodone | Hydrocodone | AH 7921 | Fentanyl |
|---|---|---|---|---|---|---|
| | | | 25% HCT | | | |
| % RE | 1% | −6% | −4% | −5% | 6% | 34% |
| % CV | 7% | 11% | 4% | 8% | 5% | 19% |
| | | | 35% HCT | | | |
| % RE | −2% | −6% | 6% | −1% | −1% | 28% |
| % CV | 11% | 4% | 2% | 4% | 11% | 20% |
| | | | 45% HCT | | | |
| % RE | −11% | 1% | −6% | −8% | −14% | 12% |
| % CV | 3% | 6% | 5% | 3% | 3% | 14% |
| | | | 55% HCT | | | |
| % RE | −10% | 1% | −4% | −5% | −31% | −5% |
| % CV | 13% | 12% | 3% | 10% | 9% | 17% |
| | | | 65% HCT | | | |
| % RE | −18% | 4% | −7% | −2% | −49% | −3% |
| % CV | 7% | 16% | 14% | 8% | 18% | 13% |

The stability of the opioids and stimulants was also tested. FIG. 4 shows the LLOQ (5 ng/mL) over 14 days stored at three different conditions:
(1) Room temperature (RT) kept in a box filled with continuous flow of nitrogen (RT+nitrogen);
(2) Room temperature (RT) kept in a glassine envelope with desiccant (RT+air); and
(3) −20° C. kept in a glassine envelope with desiccant (−20° C.+air).

The plasma volume obtained from the multilayer device was achieved and compared. In TABLE 4 above, the average Plasma/Blood volume was 0.303 µl and a standard deviation of 0.007.

The linearity and recovery of the four opioids and five stimulants were calculated. TABLE 8 below summarizes the results.

In conclusion, the validation results showed the functional benefit of the inventive multilayer device having good analytical precision, accuracy, selectivity, recovery, and sensitivity. Evaluation of the on-product stability for the nine analytes tested suggested that the multilayer device stability is compound-dependent when stored at room temperature in air. Therefore, before commercialization the on-product stability for each analyte of interest should be evaluated and appropriate instructions provided to the consumer. The benefits of this multilayer device include microsampling without the assistance of a medical professional or phlebotomist, use of a centrifuge, capability to test a wider hematocrit level range for analysis of analytes of interest such as opioids and stimulants, compatibility for a fully automated on-line LC/MS/MS analysis, and a high plasma volume yield from blood (i.e., greater than yields from commercially available methods).

TABLE 8

Linearity and Recovery of Four Opioids and Five Stimulants

| Analyte | Therapeutic Range (ng/mL plasma) | Toxic Range (ng/mL plasma) | Calibration Range (ng/mL blood) (LLOQ-ULOQ) | $r^2$ | % Recovery (±CV) LLOQ | ULOQ |
|---|---|---|---|---|---|---|
| Opioids | | | | | | |
| Morphine | 10-100 | >100 | 5-1,000 | 0.9968 | 97.6 ± 0.3 | 97 ± 0 |
| Codeine | 10-250 | >250 | 5-1,000 | 0.9988 | 97.8 ± 2 | 97 ± 0 |
| Oxycodone | 5-100 | >200 | 5-1,000 | 0.9964 | 93.2 ± 2.7 | 97.3 ± 0 |
| Hydrocodone | 10-100 | >100 | 5-1,000 | 0.9978 | 96.6 ± 2.3 | 97.5 ± 0.2 |
| Stimulants | | | | | | |
| Amphetamine | 20-150 | <200 | 5-1,000 | 0.9982 | 87.9 ± 4.5 | 94 ± 0.1 |
| Methamphetamine | 10-50 | >200 | 5-1,000 | 0.9982 | 92.4 ± 4.7 | 94.6 ± 0.1 |
| MDMA | 100-350 | >500 | 5-1,000 | 0.9969 | 93.6 ± 3.8 | 96.9 ± 0 |
| Phentermine | 30-100 | 900 | 5-1,000 | 0.9971 | 92.2 ± 4.7 | 95.7 ± 0.1 |
| Mephedrone | 50-100 | >100 | 5-1,000 | 0.9969 | 96.6 ± 0.9 | 97.5 ± 0 |

The inter-day and inter-lot accuracy and precision of four opioids and five stimulants were also determined and are shown in TABLE 9 below.

TABLE 9

| QC Level | Nominal Concentration (ng/mL) | Morphine | Codeine | Oxycodone | Hydrocodone | Amphetamine | Methamphetamine | MDMA | Phentermine | Mephedrone |
|---|---|---|---|---|---|---|---|---|---|---|
| *Inter-day - CV (%)* | | | | | | | | | | |
| LLOQ QC | 5 | 12 | 10.6 | 13.2 | 11.2 | 9.6 | 7.6 | 7.8 | 9.3 | 13.4 |
| Low QC | 15 | 7.5 | 6.1 | 9.2 | 11.3 | 6.8 | 6.3 | 6.6 | 7.7 | 11.4 |
| Med QC | 300 | 9.2 | 7.3 | 8.6 | 7.9 | 9.9 | 7.4 | 7.5 | 6.4 | 11.5 |
| High QC | 900 | 9.1 | 7.4 | 9.2 | 9.3 | 6.5 | 6.8 | 7.2 | 6.1 | 9.2 |
| *Inter-day - RE (%)* | | | | | | | | | | |
| LLOQ QC | 5 | 13.2 | −7.7 | −4.4 | 4.3 | 1.6 | 1.9 | 4 | 5.8 | 0 |
| Low QC | 15 | 4.2 | −7.8 | −6.8 | 1.6 | −3.6 | −7 | −7.7 | −2 | −3.4 |
| Med QC | 300 | 4.5 | −3.2 | −4.1 | 9.2 | −1.2 | −3.8 | −3.6 | 0.9 | 0.9 |
| High QC | 900 | 1.7 | −6.3 | −9.5 | 4 | −5.9 | −7.4 | −4.6 | −4.2 | −5.1 |
| *Inter-lot - CV (%)* | | | | | | | | | | |
| LLOQ | 5 | 14 | 10.3 | 12.9 | 11.9 | 18 | 16.9 | 8.6 | 10.2 | 15 |
| ULOQ | 1000 | 8.4 | 6.5 | 8.1 | 8.6 | 6.8 | 6.6 | 6.4 | 8.9 | 7 |

TABLE 9-continued

| QC Level | Nominal Concentration (ng/mL) | Morphine | Codeine | Oxycodone | Hydro-codone | Ampheta-mine | Metham-phetamine | MDMA | Phentermine | Mephedrone |
|---|---|---|---|---|---|---|---|---|---|---|
| | | | | | Inter-lot - RE (%) | | | | | |
| LLOQ | 5 | −10.1 | 0.5 | −5.3 | −0.6 | −13.6 | −13 | −9.3 | −2 | −9.4 |
| ULOQ | 1000 | 1.7 | −0.3 | −9.2 | −4.8 | 1.2 | 0.4 | 5.2 | −5.7 | −1.5 |

Example 3

Test Compounds for Testing Multilayer Device

The multilayer device of the invention was tested using a known hypertension and ADHD drug, guanfacine, with its [$^{13}$C, $^{15}$N$_3$] internal standard. Guanfacine ($C_9H_9Cl_2N_3O$) has a monoisotopic mass of 245.0123 Da, while the internal standard [$^{13}$C, $^{15}$N$_3$]-guanfacine ($^{13}$CC$_8$H$_9$Cl$_2$$^{15}$N$_3$O) has a monoisotopic mass of 249.0067 Da. These compounds were tested using a whole blood sample with a Blood:Plasma binding ratio (Ke/p) of 1.5 and analyzed using LC-MS/MS bioanalysis following the protocol described here.

Example 4

Method of Using Multilayer Device

As an initial matter, a fluid sample such as whole blood was collected without touching any layers sandwiched between the top cover and the bottom cover, either before or after collection, particularly avoiding the filtration membrane unit exposed through a cutout of the top cover. Even after sample collection, contact with the exposed filtration membrane unit on which the fluid sample was applied should be avoided. For finger prick or heel prick sample collection, a puncture site was selected and cleansed with 70% isopropanol. A sterile, disposable, standard lancet was used. While maintaining the finger or heel in a down position at or below heart level, the lancet pierced the cleansed site. The first drop of blood was wiped away with a sterile piece of gauze or the like. When a second, preferably large blood drop appeared, the whole blood in a volume of at least about 10 microliters to about 50 microliters, was collected by a sterile, disposable capillary tube or directly applied to the top surface of the filtration membrane unit exposed through the top cover cutout. If the cutout area of a single cutout was less than about 10 microliters, a second drop was immediately added until a sufficient volume filled the area of the cutout. Once all of the cutout circles of a single multilayer device were filled with whole blood on one side of the filtration membrane unit, the whole blood samples or specimens of the top unit were positioned in contact with the bottom unit in a closed position for about 3 minutes such that at least the filtration membrane unit, hydrophobic membrane, and collection material were intimately in contact. After about 3 minutes or longer at which time the whole blood sample was absorbed by the filtration unit and plasma collected on the collection material, the layers of the multilayer device were separated for analyte analyses. Additional time may be allowed to further dry the collected samples, preferably about 30 minutes or any amount of time for the collected samples to dry prior to analyses. For example, the collection material, once separated, was analyzed by LC/MS (liquid chromatography/mass spectroscopy), LC-MS/MS, DPS-SPE-LC-MS/MS (Dried Plasma Spot-Solid Phase Extraction-LC/MS/MS), tandem mass spectroscopy, or similar techniques for analytes, including opioids. An significant advantage of the multilayer device of the invention is its capacity to obtain multiple components from a single fluid sample and simultaneously perform multiple tests. For example, the red blood cells (RBCs) and plasma were separately collected and enzyme immunoassay (ETA) and SPE-LC-MS/MS bioanalyses were separately performed, respectively. The filtration membrane unit or portions thereof containing RBCs were analyzed by solid phase enzyme immunoassay (EIA) while the collection material containing plasma from the fluid sample were analyzed by SPE-LC-MS/MS. Briefly, the EIA procedure involved separating a filtration membrane unit comprising at least one filtration membrane layer in the form of a disk having the size, shape, and dimensions of the cutouts, where the disks contained RBCs from the multilayer device and transferring each disk to an individual microwell plate for analyses of the RBCs for analytes of interest. Multiple filtration membranes were transferred to multiple wells of a microwell plate. A diluent was added to each well and the plate incubated (O/N; 4° C.). The plate was then subjected to gentle shaking to mix and diluent. Eluant was added to each well of the microwell plate and incubated for 90 mins at 37° C. The plate was washed multiple times and an IgG-enzyme conjugate was added to each well for further incubation at 37° C. Substrate was added and incubated at 25° C. A stop solution was then added to each well to stop the reaction. The plate was then read at 405 nm and the presence of analytes of interest was determined.

Example 5

Microsampling Hematocrit-Compatible Dried Plasma Spot of Multilayer Device for Fully Automated Online DBSA-SPE-LC-MS/MS Bioanalysis of Opioids in Blood Dried blood spot (DBS) techniques known and used in the art face a limitation regarding hematocrit compatibility. Although this issue may be mitigated by the option of whole-spot versus partial-spot analyses, the ease-of-use benefit and sampling complexity since instead of microsampling, volumetric sampling would be required. Instead, a hematocrit-compatible dried plasma spot (DPS) card or multilayer device was developed that offers ease-of-use benefits and does not require complicated volumetric sampling. Essentially in this example, the multilayer device has a sandwich form of a card stock cover that, in top-down order, contains a filtration membrane unit of two filtration membranes (or red blood cell (RBC) membrane filters), a hydrophobic membrane made of polyester, a collection material that is a plasma collecting cellulose-based paper substrate, and a raised support to facilitate a direct and intimate contact for efficient wicking of plasma.

Using a single multilayer device, four spots were generated by applying an aliquot of whole blood directly onto the RBC filters followed by closure of the multilayer device if initially in the opened formation. Subsequently, the plasma collection material was removed and attached to another support that is compatible for a fully automated on-line system. The online system used included a Spark-Holland DBSA desorption system and an automated online solid-phase extraction (SPE) unit coupled to a LC-MS/MS (Shimadzu UHPLC and 8050 triple quadrupole equipped with a RAPTOR Biphenyl column, 2.7 µm, 2.1 mm×50 mm). Six analytes of interest or representative opioids including morphine, codeine, oxycodone, hydrocodone, AH 7921, fentanyl, and their corresponding deuterium-labelled analogues or internal standards were monitored SRM LC/MS positive ion electrospray ionization.

The multilayer device was used to analyze the dried plasma spots generated from whole blood from a single subject. A partial-spot option was employed using a 2 millimeter (mm) clamp. Desorption of the spots was performed with 1 milliliter (mL) elution solvent (0.1% ammonium hydroxide ($NH_4OH$) and 3% methanol (MeOH) in water) at 60° C. by flow-through desorption where a loop of 20 microliter (µl) deuterated internal standard was directly introduced to the desorption line. Subsequently, the desorption volume was loaded to a pre-conditioned SPE cartridge. LC gradient (A: 0.1% formic acid/Water and B: 100% MeOH) was used to elute the analytes from the cartridge. Preliminary results showed good linearity ($R^2$>0.990) ranging from 2 to 1,000 ng/mL for all except Fentanyl which had the range of 0.2 to 100 ng/mL, good precision (<20% CV), accuracy (<20% RE) at the lowest calibrator point (LLOQ), good selectivity as it is free of matrix effect, and extraction recovery of >90% at both the LLOQ and ULOQ. With a sampling area of only 2 mm, establishing LLOQ at low to sub ng/mL could be a challenge yet was achieved owing to the fully integrated on-line sample preparation and analysis system described.

Preliminary data also showed successful red blood cell filtration to generate hemolysis-free plasma spots at HCT levels ranging from about 25% to about 65%. Although spectrophotometric assays had not been conducted, hemolysis-free plasma spots generated from this novel multilayer device was contemplated to also be used for such assays. Unlike whole blood, plasma spot homogeneity is independent of HCT level. Thus, analysis of the spots produced from various HCT levels can be carried out using partial spot analysis and thus volumetric sampling is not required. This multilayer device was used for flexible sampling volumes, including those ranging from about 10 µL to about 50 µL of whole blood by adjusting the RBC filter size accordingly.

Example 6

Automated Flow-Through Elution Coupled with on-Line SPE-LC-MS/MS Bioanalysis of Analytes Using a Multilayer Device Precision, accuracy, stability, spot elution positions, and plasma volume generated using a whole blood fluid sample applied to a multilayer device were tested.

Chemicals, reagents, and materials: Morphine, [$^2H_3$]-morphine, codeine, [$^2H_3$]-codeine, oxycodone, [$^2H$]-oxycodone, hydrocodone, [$^2H_3$]-hydrocodone, amphetamine, [$^2H_5$] amphetamine, methamphetamine, [$^2H_5$] methamphetamine, MDMA, [$^2H_5$]-MDMA, phentermine, [$^2H_5$]-phentermine, mephedrone, and [$^2H_3$]-mephedrone were purchased from CERILLIANT™ (Round Rock, TX USA). LC-MS grade solvents: acetonitrile (ACN), isopropanol (IPA), and methanol (MeOH) were purchased from Honeywell Burdick & Jackson (Muskegon, MI, USA). Milli Q water was obtained from an in house MILLIPORE® system. Ammonium formate, ammonium hydroxide, and formic acid (FA) were obtained from EMD) Chemicals Inc. (Gibbstown, NJ, USA). Human blood samples were collected from healthy volunteers in $Na_2EDTA$ treated Monoject™ tubes, stored at −4° C. and used within four days from the point of withdrawing. Stock and working solutions were prepared and stored in 4 mL borosilicate amber glass vials from Kimble Chase (Vineland, NJ USA). Blood samples were prepared in 1.5 mL Protein LoBind tubes from EPPENDORF® (Hamburg, Germany). Volumetric pipettes were Pipet-Lite XLS series from RAININ® Instrument LLC (Oakland, CA, USA). Materials and craft tools used for manufacturing the book-type multilayer device were purchased from Amazon except for the following: Perkin Elmer 226 cards which were purchased from Perkin Elmer (Boston, MA, USA), folded card stocks (50.8 mm (length)×76.2 mm (width)) were from Cards and Pockets (South Easton, MA, USA). Grade 601 cellulose paper substrate and Hollytex®3256 polyester membrane (referred to later here as a polyester layer) were donated by AHLSTROM® Filtration, LLC (Mt Holly Springs, PA, USA) and iPOC$^{DX}$™ membrane filters were donated by International Point of Care Inc. (Toronto, Ontario, Canada).

Preparation of working solutions: Opioid and stimulant standards and their deuterated analogs were purchased in 1 mg/mL and 0.1 mg/mL methanolic solutions, respectively. Calibrator and QC working solutions were prepared by dilution of the primary stocks with MeOH:H2O (3:7 v/v) yielding 0.25 µg/mL, 0.50 µg/mL, 1.25 µg/mL, 2.50 µg/mL, 5.00 µg/mL, 12.5 µg/mL, 25.0 µg/mL, and 50.0 µg/mL for the 8-point calibrators and 0.25 µg/mL, 0.75 µg/mL, 15 µg/mL, 45 µg/mL for the 4 QC levels. Deuterated internal standard (IS) solution was a mixture of 5 ng/mL [$^2H_3$]-morphine, 4 ng/mL [$^2H_3$]-codeine, 2.5 ng/mL [$^2H_6$]-oxycodone, 2.5 ng/mL [$^2H_3$] hydrocodone 10 ng/mL [$^2H_5$]-amphetamine, 10 ng/mL [$^2H_5$] methamphetamine, 10 ng/mL [$^2H_5$]-MDMA, 10 ng/mL [$^2H_5$]-phentermine, and 10 ng/mL [$2H_3$]-mephedrone in MeOH:$H_2O$ (3:7 v/v). All solutions were stored at −20° C.

Linearity, precision, accuracy, and recovery: In a batch analysis, a set of eight calibrators was analyzed at the beginning and another set at the end of the batch. In between the two sets, four QC levels (n=6) and recovery samples (n=2) were analyzed. Using whole blood of the same volunteer, this analysis was repeated on three different days to obtain intra- and inter-day precision and accuracy values. The automated platform of a flow-through spot elution cannot adopt the conventional approach of recovery determination. To circumvent this, extraction recovery was determined by repeatedly eluting or extracting the same spot for five successive times at the LLOQ and 10 times at ULOQ. Recovery was calculated by (analyte peak area of the first extraction/sum of 5 or 10 extractions)×100. This provided a relative extraction recovery in the absence of the on-line SPE recovery. Calibration curves (n=2) were plotted using analyte/IS peak area ratio and observed to have linearity of $R^2 \geq 0.963$ over the quantitative range using $1/x^2$ weighted linear regression (TABLE 8).

The curve range covers both the therapeutic and toxic ranges for the title compounds (Regenthal, R., et al. *J Clin Monit Comput* 1999, 15, 529-544; Schulz, M., et al. *Critical Care* 2012, 16, R136-R136). In DBS and DPS analyses, introduction of IS can be performed in various ways as described previously (Abu-Rabie, P., et al. *Analytical Chemistry* 2015, 87, 4996-5003; van Baar, B. L., et al. *Bioanalysis* 2013, 5, 2137-2145). In this example, the IS was introduced to the flow-through elution solvent; hence, the internal standard (IS) could not compensate for any on card extraction discrepancies such as analyte recovery bias and Hct related recovery bias. One way to circumvent this issue was to optimize assay recovery as noted by Abu-Rabie et al. (op. cit.) reporting no observable Hct-related recovery bias for assay recovery of over 90%. Recovery for this assay was ≥90.0% for all except for amphetamine which was 87.8% as shown in TABLE 8. Intra-day precision and accuracy results also showed acceptable values (TABLE 11). Inter-day precision and accuracy were calculated using the average intra-day values (n=3) and results showed passing the acceptable criteria at all QC levels for all nine analytes except for codeine at the LLOQ QC level which was 23% (TABLE 9).

Linearity was also tested with morphine, codeine, oxycodone, hydrocodone, and AH 7921 with a calibration range of 2 ng/mL to 1.000 ng/mL. Fentanyl was also tested and found to have linearity. The fentanyl calibration range was from 0.2 ng/mL to 100 ng/mL. FIG. 9 shows linearity graphs for morphine and fentanyl. Codeine, oxycodone, hydrocodone, and AH 7921 were observed as having similar linearity as that of morphine. TABLE 10 below shows the $R^2$ values for each tested compound.

TABLE 10

| Compound | $R^2$ |
|---|---|
| Morphine | 0.9996 |
| Codeine | 0.9996 |
| Oxycodone | 0.9988 |
| Hydrocodone | 0.9984 |
| AH 7921 | 0.9968 |
| Fentanyl | 0.9983 |

Selectivity and carry-over: Selectivity was assessed by evaluating the double blank (matrix blank without IS), blank (matrix blank with IS), and fortified samples at the LLOQ (5 ng/mL) and ULOQ (1000 ng/mL) levels from six individual matrix lots (six different human whole bloods). To evaluate carry-over effects, two blank samples (blank card without plasma spots) were analyzed after the ULOQ. As shown in FIG. 7, the double blank sample showed negligible carry-over IS signals (about 1% of the total IS intensity) while blank sample showed non-detectable analyte signals. Good chromatographic resolution and detection were observed at the LLOQ level for all nine analytes. Separation of isomers codeine and hydrocodone and isomers methamphetamine and phentermine may be observed. Inter-lot precision and accuracy at LLOQ and ULOQ were within the acceptance criteria for all analytes (TABLE 9). Carry-over was evaluated by running a blank spot (a blank card with no sample spot) after the ULOQ calibrator. Unacceptable (≥20% of the LLOQ signal intensity) carry-over signals were observed for amphetamine, methamphetamine, MDMA, and phentermine. A variety of solvent washes and procedures were tried and results showed improvement but failed to reduce the carry-over to the acceptable levels. Thus, the carry-over issue was mitigated by employing two sequential blanks (no plasma spot) after the ULOQ calibrator. With the wash procedure, the LC MS/MS cycle time per run increased from 4.3 to 6.2 min.

Flexible volumetric sampling was performed from 20 µl, 30 µl, and 50 µl whole blood. The tested opioids were morphine, codeine, oxycodone, hydrocodone, AH 7921, and Fentanyl. Calibration curve was prepared using 30 µL whole blood. Fortified level was at LLOQ QC (2 ng/mL or 0.2 ng/mL). FIG. 10 and FIG. 11 show the results of testing for flexible volumetric samplings from 20 µl-50 µl. The opioid concentrations of each of the opioids at the varying whole blood sample volumes—20 µl, 30 µl, and 50 µl (columns left to right for each opioid)—of FIG. 10 were shown to be similar for morphine, codeine, oxycodone, hydrocodone, and AH 7921, but fentanyl had a much lower concentration in all of the volumes. FIG. 11 shows that the precision and accuracy at LLOQ QC passed the required criteria at +20% for relative error (RE) and 20% for coefficient of variance (CV) for (A) 20 µl, (B) 30 µl, and (C) 50 µl whole blood.

Example 7

Automated Flow-Through Elution Coupled with on-Line SPE-LC-MS/MS Bioanalysis of Analytes Using a Multilayer Device A dried plasma spot generated from application of whole blood to a multilayer device described here allowed red blood cell (RBC) filtration which generated plasma from a simple point-of-care sample collection and without the need for centrifugation. A multilayer device for automated analysis of analytes of interest in a whole blood fluid sample was developed and validated by employing fully automated flow-through elution coupled with on-line SPE-LC-ESI-MS/MS. The quantitative determination of four representative analytes of interest included opioids (Morphine, Codeine, Oxycodone, Hydrocodone) and five stimulants (Amphetamine, Methamphetamine, 3,4-Methylenedioxymethamphetamine (MDMA), Phentermine, and Mephedrone) and in one method using their corresponding deuterium labeled analogues as internal standards. Method validation results showed good linearity ($R^2 \geq 0.9963$) ranging from about 5 to about 1,000 ng/mL Intra-day and inter-day precision and accuracy were within the acceptable limits at four quality control (QC) levels. Extraction recovery was ≥87.9% at both the lower limit of quantitation (LLOQ) and the upper limit of quantitation (ULOQ) along with acceptable selectivity and sensitivity. DPS on-card short-term stability was compound-dependent and storage-dependent. The additional benefits of the validated book-type multilayer device include a wider applicability range of Hct (30% to 60%), automated on-line analysis compatibility, a higher plasma volume yield, and a feature of flexible sampling volume.

TABLE 11

| QC Level | Morphine | Codeine | Oxycodone | Hydrocodone | Amphetamine | Methamphetamine | MDMA | Phentermine | Mephedrone |
|---|---|---|---|---|---|---|---|---|---|
| Intra-day Precision and Accuracy of Four Opioids and Five Stimulants | | | | | | | | | |
| Day 1 Precision - CV (%) | | | | | | | | | |
| LLOQ QC | 9.6% | 6.9% | 6.9% | 13.2% | 6.8% | 4.9% | 9.3% | 3.7% | 7.9% |
| Low QC | 9.9% | 6.0% | 8.3% | 9.2% | 5.8% | 5.8% | 4.5% | 8.2% | 6.8% |
| Med QC | 11.3% | 7.6% | 7.2% | 8.8% | 7.6% | 8.1% | 9.6% | 6.4% | 7.3% |
| High QC | 13.0% | 11.4% | 10.8% | 11.9% | 9.5% | 11.2% | 11.4% | 9.6% | 13.2% |
| Day 1 Accuracy - RE (%) | | | | | | | | | |
| LLOQ QC | -0.3% | -10.2% | -3.3% | 7.2% | -4.7% | -3.8% | 0.7% | -3.0% | -6.0% |
| Low QC | 4.7% | -5.4% | -5.4% | 6.1% | -3.2% | -4.6% | -4.0% | 0.2% | -4.2% |
| Med QC | 9.5% | 1.4% | -1.8% | 12.4% | 0.5% | -2.0% | -0.9% | 4.1% | 2.9% |
| High QC | 1.8% | -3.6% | -5.2% | 7.1% | -3.6% | -7.6% | -2.7% | -3.7% | -1.2% |
| Day 2 Precision - CV (%) | | | | | | | | | |
| LLOQ QC | 7.6% | 9.5% | 20.5% | 10.7% | 11.8% | 9.8% | 9.8% | 8.4% | 8.4% |
| Low QC | 8.0% | 6.1% | 11.7% | 11.1% | 7.8% | 8.6% | 5.8% | 10.2% | 11.3% |
| Med QC | 9.1% | 7.9% | 12.4% | 8.3% | 13.7% | 9.9% | 8.5% | 7.6% | 15.0% |
| High QC | 7.3% | 3.2% | 7.0% | 7.0% | 2.9% | 4.8% | 4.3% | 4.0% | 7.5% |
| Day 2 Accuracy - RE (%) | | | | | | | | | |
| LLOQ QC | 15.0% | -5.2% | -5.5% | 6.5% | -0.2% | 3.0% | 6.4% | 3.6% | 13.5% |
| Low QC | 6.0% | -6.2% | -3.0% | 5.8% | 0.7% | -9.1% | -6.2% | -3.7% | 6.8% |
| Med QC | 5.4% | -3.5% | -2.5% | 11.8% | 5.6% | -1.9% | -2.9% | -1.9% | 9.9% |
| High QC | 4.4% | -8.8% | -15.1% | 0.0% | -4.7% | -7.4% | -5.2% | -5.4% | -7.7% |
| Day 3 Precision - CV (%) | | | | | | | | | |
| LLOQ QC | 9.5% | 11.7% | 9.3% | 10.6% | 5.2% | 4.9% | 3.8% | 5.0% | 9.4% |
| Low QC | 4.5% | 4.7% | 6.1% | 10.4% | 4.7% | 4.6% | 6.1% | 5.2% | 8.0% |
| Med QC | 5.1% | 4.8% | 7.1% | 6.1% | 4.1% | 4.8% | 4.2% | 5.4% | 6.2% |
| High QC | 7.8% | 6.6% | 8.0% | 9.9% | 5.0% | 5.4% | 6.0% | 5.3% | 6.9% |
| Day 3 Accuracy - RE (%) | | | | | | | | | |
| LLOQ QC | 20.0% | -8.2% | -4.2% | -0.3% | 8.6% | 5.6% | 4.3% | 15.3% | -8.4% |
| Low QC | 2.2% | -11.5% | -11.2% | -6.3% | -7.6% | -7.7% | -12.8% | -2.7% | -11.2% |
| Med QC | -0.4% | -6.9% | -7.0% | 4.8% | -7.2% | -6.5% | -6.4% | -0.1% | -6.6% |
| High QC | -1.7% | -6.9% | -9.4% | 4.1% | -9.5% | -7.0% | -6.2% | -3.7% | -6.8% |

Example 8

Analysis of RBC and Reticulocyte Surface Proteins Using the Multilayer Device

A filtration membrane disk in the top unit of the multilayer device containing red blood cells and their precursors was removed from the top unit and analyzed for proteins and other constituents of the filtration membrane using immunoassay or LC-MS/MS techniques. After removing the filtration membrane disk from the multilayer device, a portion of the disk or an entire filtration membrane disk was covered with an ethanolic buffer solution and placed in a sonicator for a sufficient length of time to remove soluble proteins. Membrane-bound proteins such as, but not limited to, Band 3 or transferrin receptor were released from the filtration membrane after digestion with a protease enzyme, and the resulting peptides were analyzed quantitatively by LC-MS/MS.

Similar approaches known and used in the art can be used to quantify intracellular proteins.

The ability to collect dried cellular components in remote locations and quantify the cell surface proteins affords a significant advantage over other sample collection technologies. For example, reticulocyte maturation changes observed during the storage of a liquid sample of blood are avoided using the dried blood technique described here.

Examples of the invention may also include:

1. A dried plasma spot card comprising: a card stock; and a plasma collection substrate coupled to the card stock and comprising a polyester membrane to enhance uniformity of a collected blood sample.

2. The dried plasma spot card of Card 1, wherein the paper plasma collection substrate controls concentration distribution of the collected blood sample.

3. The dried plasma spot card of Card 2, wherein the concentration distribution is based on a difference between a center and peripheral position of the collected blood sample.

4. The dried plasma spot card of Card 1, wherein the collected blood sample is collected for determining a hematocrit of the collected blood sample.

5. The dried plasma spot card of Card 1, wherein the plasma collection substrate has a first end and a second end.

6. The dried plasma spot card of Card 5, wherein the paper plasma collection substrate bows outward relative to the card stock such that only the first and second ends are coupled to the card stock and an inner region of the substrate is separated from the card stock.

7. A method comprising: providing a dried plasma spot card that comprises: a card stock: and a plasma collection substrate coupled to the card stock and comprising a polyester membrane to enhance uniformity of a collected blood sample; collecting a blood sample on the plasma collection substrate; and analyzing the collected blood sample for an opioid.

8. The method of Method 7, wherein the paper plasma collection substrate controls a concentration distribution of the collected blood sample.

9. The method of Method 8, wherein the concentration distribution is based on a difference between a center and peripheral position of the collected blood sample.

10. The method of Method 7, further comprising determining a hematocrit of the collected blood sample.

11. The method of Method 7, wherein the plasma collection substrate has a first end and a second end.

12. The method of Method 11, wherein the paper plasma collection substrate bows outward relative to the card stock such that only the first and second ends are coupled to the card stock and an inner region of the substrate is separated from the card stock.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

The content of all patents, patent applications, published articles, abstracts, books, reference manuals, abstracts, and the like, as cited here are all incorporated by reference in their entireties to more fully describe the state of the art to which the disclosure pertains.

One or more features from any embodiment may be combined with one or more features of any other embodiment without departing from the scope of the invention. A recitation of "a", "an" or "the" is intended to mean "one or more" unless specifically indicated to the contrary. Recitation of "and/or" is intended to represent the most inclusive sense of the term unless specifically indicated to the contrary.

One or more of the elements of the present system may be claimed as means for accomplishing a particular function. Where such means-plus-function elements are used to describe certain elements of a claimed system it will be understood by those of ordinary skill in the art having the present specification, figures and claims before them, that the corresponding structure is a general purpose computer, processor, or microprocessor (as the case may be) programmed to perform the particularly recited function using functionality found in any general purpose computer without special programming and/or by implementing one or more algorithms to achieve the recited functionality. As would be understood by those of ordinary skill in the art that algorithm may be expressed within this disclosure as a mathematical formula, a flow chart, a narrative, and/or in any other manner that provides sufficient structure for those of ordinary skill in the art to implement the recited process and its equivalents.

While the present disclosure may be embodied in many different forms, the drawings and discussion are presented with the understanding that the present disclosure is an exemplification of the principles of one or more inventions and is not intended to limit any one of the inventions to the embodiments illustrated.

The present disclosure provides a solution to the long-felt need described above. In particular, systems and methods described herein may be configured to improve management of health care service providers. Further advantages and modifications of the above described system and method will readily occur to those skilled in the art. The disclosure, in its broader aspects, is therefore not limited to the specific details, representative system and methods, and illustrative examples shown and described above. Various modifications and variations can be made to the above specification without departing from the scope or spirit of the present disclosure, and it is intended that the present disclosure covers all such modifications and variations provided they come within the scope of the following claims and their equivalents.

What is claimed:

1. A sample collection device comprising:
    a top unit including one or more orifices for receiving a liquid sample; and
    a bottom unit including a collection material and a bottom cover having a top surface and a bottom surface; and
    one or more filter membranes each having a diameter that is less than or equal to a diameter of each of the one or more orifices in the top unit and disposed within each of the one or more orifices in the top unit,
    wherein the top unit is adjacent to and connected to the bottom unit via a hinged edge,
    wherein the collection material has a bottom surface disposed adjacent to the top surface of the bottom cover, and
    wherein the collection material is disposed so as to receive the liquid sample received through the one or more orifices in the top unit.

2. The sample collection device of claim 1, wherein the bottom surface of the collection material is adhered to the top surface of the bottom cover.

3. The sample collection device of claim 1 further comprising a hydrophobic membrane disposed between the collection material and the top unit.

4. The sample collection device of claim 1, wherein the collection material is configured to receive the liquid sample and store the liquid sample as one or more dried sample spots.

5. The sample collection device of claim 1, wherein the top unit and the bottom unit are tamper-proof when in a closed position.

6. A method of sample collection, the method comprising:
    providing a sample collection device including:
        a top unit including one or more orifices for receiving a liquid sample;
        a bottom unit including a collection material and a bottom cover having a top surface and a bottom surface, bottom unit is adjacent to and connected to the top unit via a hinged edge, wherein the collection material has a bottom surface disposed adjacent to the top surface of the bottom cover, and wherein the collection material is disposed so as to receive the liquid sample received through the one or more orifices in the top unit; and
        one or more filter membranes each disposed within each of the one or more orifices in the top unit;

receiving one or more liquid samples through the one or more orifices in the top unit;

allowing the one or more liquid samples to dry on the collection material into one or more dried sample spots; and performing one or more chemical analyses with the dried sample spots.

7. The method of claim 6 further comprising allowing the one or more liquid samples to incubate on the collection material at room temperature for about three minutes.

8. The method of claim 6 further comprising removing the collection material from the bottom unit.

9. The method of claim 6 further comprising storing the collection material with an inert gas.

10. The method of claim 6, wherein the receiving one or more liquid samples includes receiving at least 20 microliters of one of blood, red blood cells, plasma, platelets, saliva, tears, amniotic fluid, semen, or urine.

11. The method of claim 6, wherein the bottom surface of the collection material is adhered to the top surface of the bottom cover.

12. The method of claim 6, wherein further a hydrophobic membrane is disposed between the collection material and the top unit.

13. The method of claim 6 further comprising filtering the one or more liquid samples through the one or more filter membranes.

14. The method of claim 6, wherein a diameter of each of the one or more filter membranes is less than or equal to a diameter of each of the one or more orifices in the top unit.

15. A sample collection device comprising:

a top unit including one or more orifices for receiving a liquid sample;

a bottom unit including a collection material and a bottom cover having a top surface and a bottom surface;

a hydrophobic membrane disposed between the collection material and the top unit; and one or more filter membranes each disposed within each of the one or more orifices in the top unit, wherein the top unit is adjacent to and connected to the bottom unit via a hinged edge, wherein the collection material has a bottom surface disposed adjacent to the top surface of the bottom cover, and wherein the collection material is disposed so as to receive the liquid sample received through the one or more orifices in the top unit.

* * * * *